(12) United States Patent
Nakano et al.

(10) Patent No.: US 12,393,781 B2
(45) Date of Patent: Aug. 19, 2025

(54) INFORMATION PROCESSING APPARATUS, OPERATION METHOD OF INFORMATION PROCESSING APPARATUS, AND OPERATION PROGRAM OF INFORMATION PROCESSING APPARATUS

(71) Applicant: FUJIFILM Corporation, Tokyo (JP)

(72) Inventors: Norihisa Nakano, Tokyo (JP); Ryota Ozaki, Tokyo (JP); Tomoko Ohkuma, Tokyo (JP); Tomoki Taniguchi, Tokyo (JP); Yuki Tagawa, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 281 days.

(21) Appl. No.: 18/063,073

(22) Filed: Dec. 7, 2022

(65) Prior Publication Data
US 2023/0205997 A1 Jun. 29, 2023

(30) Foreign Application Priority Data
Dec. 27, 2021 (JP) .................................. 2021-213437

(51) Int. Cl.
G06F 17/27 (2006.01)
G06F 40/295 (2020.01)
G16H 15/00 (2018.01)
G06F 40/30 (2020.01)

(52) U.S. Cl.
CPC ........... *G06F 40/295* (2020.01); *G16H 15/00* (2018.01); *G06F 40/30* (2020.01)

(58) Field of Classification Search
CPC .... G06F 40/284; G06F 40/279; G06F 40/295; G06F 40/289; G06F 40/30; G16H 15/00; G16H 50/20

USPC ............................................................. 704/9
See application file for complete search history.

(56) References Cited

U.S. PATENT DOCUMENTS

| | | | |
|---|---|---|---|
| 2011/0196698 A1* | 8/2011 | Benja-Athon | G16H 50/20 |
| | | | 705/2 |
| 2021/0182490 A1* | 6/2021 | Guo | G06F 40/284 |
| 2021/0200949 A1 | 7/2021 | Gao et al. | |
| 2022/0382979 A1* | 12/2022 | Klein | G06F 40/284 |

FOREIGN PATENT DOCUMENTS

| | | | |
|---|---|---|---|
| CN | 113821601 A | * | 12/2021 |
| JP | 2021111323 | | 8/2021 |
| JP | 2021140483 | | 9/2021 |

OTHER PUBLICATIONS

Chen Lin et al., "Entity BERT: Entity-centric Masking Strategy for Model Pretraining for the Clinical Domain", Proceedings of the BioNLP 2021 workshop, p. 191-201, Jun. 11, 2021.
"Notice of Reasons for Refusal of Japann Counterpart Application No. 2021-213437", issued on May 27, 2025, with English translation thereof, p. 1-p. 5.

* cited by examiner

*Primary Examiner* — Md S Elahee
(74) *Attorney, Agent, or Firm* — JCIPRNET

(57) ABSTRACT

A CPU of a training data creation apparatus includes an extraction unit, a derivation unit, and a creation unit. The extraction unit extracts a plurality of unique expressions that are specific term phrases from a medical document. The derivation unit derives a degree of association indicating a degree of association among the plurality of unique expressions. The creation unit selects a target term phrase that is a term phrase as a target to be masked.

15 Claims, 24 Drawing Sheets

FIG. 8

DEGREE OF ASSOCIATION INFORMATION — 42

| COMBINATION OF TYPES | DEGREE OF ASSOCIATION |
|---|---|
| PROPERTY OF LESION-DISEASE NAME | 10 |
| LESION NAME-DISEASE NAME | 9 |
| ANATOMICAL SITE-LESION NAME | 8 |
| ANATOMICAL SITE-DISEASE NAME | 8 |
| ⋮ | |
| QUANTITY-LESION NAME | 1 |
| QUANTITY-PROPERTY OF LESION | 0 |

SET IN ADVANCE BY OPERATOR

FIG. 9

DERIVATION RESULT — 61

| COMBINATION OF UNIQUE EXPRESSIONS (COMBINATION OF TYPES) | DEGREE OF ASSOCIATION |
|---|---|
| LIVER S3-SIZE OF DIAMETER OF 6 cm (ANATOMICAL SITE-QUANTITY) | 1 |
| LIVER S3-TUMOR (ANATOMICAL SITE-LESION NAME) | 8 |
| ⋮ | |
| TUMOR-HCC (LESION NAME-DISEASE NAME) | 9 |
| ⋮ | |
| SIZE OF DIAMETER OF 6 cm-EARLY ENHANCEMENT (QUANTITY-PROPERTY OF LESION) | 0 |
| SIZE OF DIAMETER OF 6 cm-washout (QUANTITY-PROPERTY OF LESION) | 0 |
| ⋮ | |
| EARLY ENHANCEMENT-HCC (PROPERTY OF LESION-DISEASE NAME) | 10 |
| washout-HCC (PROPERTY OF LESION-DISEASE NAME) | 10 |

FIG. 10

| SELECTION CONDITION | — 43 |

1. 15% OF TOKENS ARE MASKED
2. AT LEAST ONE UNIQUE EXPRESSION IS SELECTED
3. AT LEAST ONE UNIQUE EXPRESSION OF WHICH DEGREE OF ASSOCIATION IS GREATER THAN OR EQUAL TO 8 IS EXCLUDED FROM CANDIDATES OF TARGET TERM PHRASE

INFORMATION PROCESSING APPARATUS, OPERATION METHOD OF INFORMATION PROCESSING APPARATUS, AND OPERATION PROGRAM OF INFORMATION PROCESSING APPARATUS

CROSS-REFERENCE TO RELATED APPLICATIONS

The present application claims priority under 35 U.S.C. § 119 to Japanese Patent Application No., 2021-213437 filed on Dec. 27, 2021. The above application is hereby expressly incorporated by reference, in its entirety, into the present application.

BACKGROUND

1. Technical Field

The disclosed technology relates to an information processing apparatus, an operation method of an information processing apparatus, and an operation program of an information processing apparatus.

2. Description of the Related Art

In the field of natural language processing (NLP), attention has been paid to bidirectional encoder representations from transformers (BERT) using a transformer encoder. In BERT, masked language modeling (MLM) is performed as pretraining. MLM is a so-called cloze test for predicting which term phrase fits in a masked part of a training input text in which a part of term phrases is masked. After such pretraining, fine tuning corresponding to a desired natural language processing task is performed in BERT. The term phrase is a single term (word) and/or a phrase consisting of a combination of one or more single terms.

Typically, a term phrase (hereinafter, referred to as a target term phrase) that is a target to be masked in the training input text used in MLM is randomly selected. However, in this case, a term phrase that is not important in a target document of the natural language processing task is often selected as the target term phrase. Performing MLM using such a training input text loses a training opportunity for an important term phrase in the target document of the natural language processing task. Thus, there is a concern that effective pretraining is not performed.

Particularly, in a field such as the medical field in which it is difficult to obtain a large amount of documents as a base of the training input text, the concern that the effective pretraining is not performed is increased because of the loss of the training opportunity for the important term phrase. For example, in a text "Early enhancement is recognized in a tumor found in a liver S3.", in a case where a term phrase such as a preposition "in" that is not important is selected as the target term phrase, and an important term phrase such as "tumor" or "early enhancement" is not selected as the target term phrase, the training opportunity for the important term phrase is lost, and the effective pretraining is not performed. Therefore, for example, a method for studying how to select the target term phrase has been suggested as in Chen Lin, et al: EntityBERT: Entity-centric Masking Strategy for Model Pretraining for the Clinical Domain, Proceedings of the BioNLP 2021 workshop, pages 191-201 Chen Lin, et al: EntityBERT: Entity-centric Masking Strategy for Model Pretraining for the Clinical Domain, Proceedings of the BioNLP 2021 workshop, pages 191-201 Jun. 11, 2021 discloses a technology for creating a training input text used in MLM of BERT that targets medical documents. Specifically, a unique expression that is a term phrase such as a disorder, a sign, a symptom, a drug, an anatomical site, a procedure, and a time expression unique to a medical document is extracted, and the target term phrase is selected based on the extracted unique expression.

SUMMARY

In a case where a term phrase necessary for predicting the masked term phrase is not present in the training input text used in MLM, it is apparently difficult to predict the masked term phrase. For example, in the medical document, the early enhancement that is a term representing a property of a tumor of a liver is a term highly related to hepatocellular carcinoma (HCC). However, in a case where both of "early enhancement" and "HCC" in a text "Early enhancement is recognized in a tumor found in a liver S3. HCC is suspected." are masked, terms necessary for predicting "early enhancement" and "HCC" from each other are not present in the text. Thus, it is difficult to predict one of "early enhancement" and "HCC" from the other. This problem is not considered in Chen Lin, et al: EntityBERT: Entity-centric Masking Strategy for Model Pretraining for the Clinical Domain, Proceedings of the BioNLP 2021 workshop, pages 191-201 Jun. 11, 2021. Accordingly, there is still a concern that the effective pretraining is not performed.

One embodiment according to the disclosed technology provides an information processing apparatus, an operation method of an information processing apparatus, and an operation program of an information processing apparatus that can create a training input text contributing to effective training of a natural language processing model.

An information processing apparatus according to an aspect of the present disclosure is an information processing apparatus that creates a training input text which is used for training a natural language processing model and in which a part of term phrases is masked, from a document, the information processing apparatus comprising a processor, in which the processor is configured to extract a plurality of specific term phrases from the document, derive a degree of association indicating a degree of association among the plurality of specific term phrases, and select a target term phrase that is a term phrase as a target to be masked based on the degree of association.

It is preferable that the processor is configured to exclude the specific term phrase of which the degree of association with the term phrase selected as the target term phrase satisfies a condition set in advance, from candidates of the target term phrase.

It is preferable that the processor is configured to determine a text of the same type as a text including the term phrase selected as the target term phrase, and use the text including the target term phrase and the text of the same type as the training input text.

It is preferable that the processor is configured to determine that a text including the specific term phrase of which the degree of association with the term phrase selected as the target term phrase satisfies a condition set in advance is the text of the same type.

It is preferable that the document is a medical document, and the processor is configured to determine that a text describing the same organ as an organ related to the term phrase selected as the target term phrase is the text of the same type.

It is preferable that the processor is configured to derive the degree of association using degree-of-association information in which the degree of association corresponding to a combination of types of the specific term phrases is set in advance.

It is preferable that the document is a medical document, and the types include at least one of an anatomical site, a quantity, a lesion name, a property of a lesion, or a disease name.

It is preferable that the processor is configured to derive the degree of association using a trained derivation model.

It is preferable that the derivation model is created based on a trained natural language processing model.

It is preferable that the processor is configured to train the natural language processing model using the training input text.

It is preferable that the processor is configured to repeat a cycle of a series of processing including creating an extraction model for extracting at least the specific term phrases from the natural language processing model, creating a training document from which the specific term phrases are extracted using the extraction model, creating the training input text from the training document, and updating the natural language processing model by training the natural language processing model using the created training input text.

It is preferable that the processor is configured to, in an initial cycle, create the extraction model from a natural language processing model created by training using a training input text in which the target term phrase is randomly selected regardless of the degree of association.

It is preferable that the processor is configured to further create a derivation model for deriving the degree of association from the natural language processing model, and create the training document labeled with the degree of association using the derivation model.

It is preferable that the document is a medical document, and the processor is configured to further create a determination model for determining which organ a text describes from the natural language processing model, and create the training document labeled with the organ using the determination model.

An operation method of an information processing apparatus according to another aspect of the present disclosure is an operation method of an information processing apparatus that creates a training input text which is used for training a natural language processing model and in which a part of term phrases is masked, from a document, the operation method comprising extracting a plurality of specific term phrases from the document, deriving a degree of association indicating a degree of association among the plurality of specific term phrases, and selecting a target term phrase that is a term phrase as a target to be masked based on the degree of association.

An operation program of an information processing apparatus according to still another aspect of the present disclosure is an operation program of an information processing apparatus that creates a training input text which is used for training a natural language processing model and in which a part of term phrases is masked, from a document, the operation program causing a computer to execute a process comprising extracting a plurality of specific term phrases from the document, deriving a degree of association indicating a degree of association among the plurality of specific term phrases, and selecting a target term phrase that is a term phrase as a target to be masked based on the degree of association.

According to the disclosed technology, an information processing apparatus, an operation method of an information processing apparatus, and an operation program of an information processing apparatus that can create a training input text contributing to effective training of a natural language processing model can be provided.

BRIEF DESCRIPTION OF THE DRAWINGS

Exemplary embodiments according to the technique of the present disclosure will be described in detail based on the following figures, wherein:

FIG. 8 is a diagram illustrating degree-of-association information;

FIG. 9 is a diagram illustrating a derivation result;

FIG. 10 is a diagram illustrating a selection condition;

DETAILED DESCRIPTION

Embodiment 1

Figure 1:
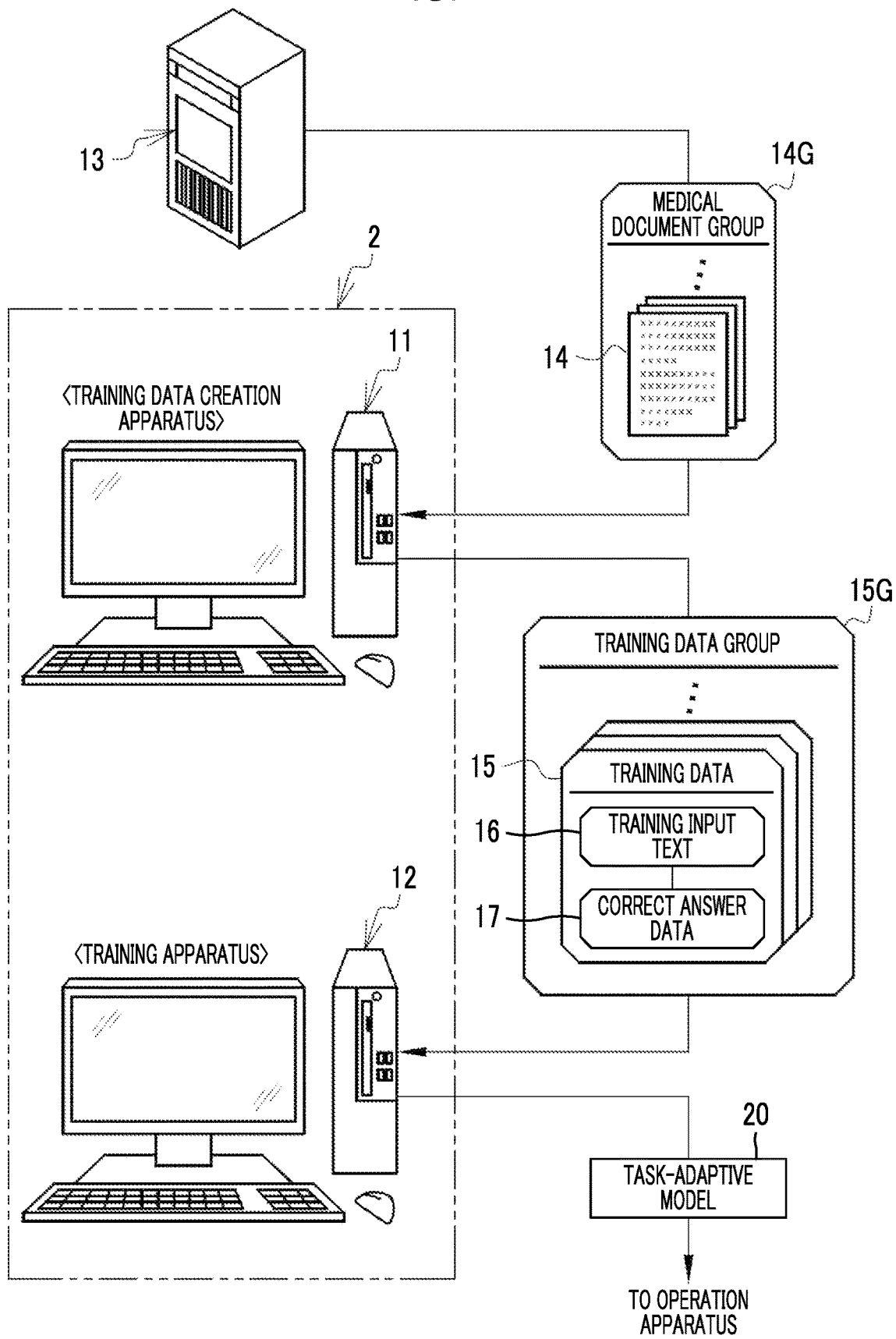
FIG. 1 is a diagram illustrating a training system and the like including a training data creation apparatus and a training apparatus.

As illustrated in FIG. 1 as an example, a training system 2 is a system for training a natural language processing model 10 (refer to FIG. 3) that is BERT using a transformer encoder, and is composed of a training data creation apparatus 11 and a training apparatus 12. For example, the training data creation apparatus 11 and the training apparatus 12 are desktop personal computers or workstations. The training data creation apparatus 11 and the training apparatus 12 are connected through a network (not illustrated) such as the Internet. The training data creation apparatus 11 and the training apparatus 12 are an example of an "information processing apparatus" according to an embodiment of the disclosed technology.

A medical document data base (hereinafter, abbreviated to DB) server 13 is connected to the training data creation apparatus 11 through the network (not illustrated) such as the Internet. The training data creation apparatus 11 receives a medical document group 14G from the medical document DB server 13. The medical document group 14G is a collection of a plurality of medical documents 14 such as a medical paper and a radiologic interpretation report.

The training data creation apparatus 11 creates a plurality of pieces of training data 15 from the medical document 14. The training data 15 is a set of a training input text 16 and correct answer data 17. The training data creation apparatus 11 distributes a training data group 15G that is a collection of the plurality of pieces of the training data 15 to the training apparatus 12.

Figure 2:
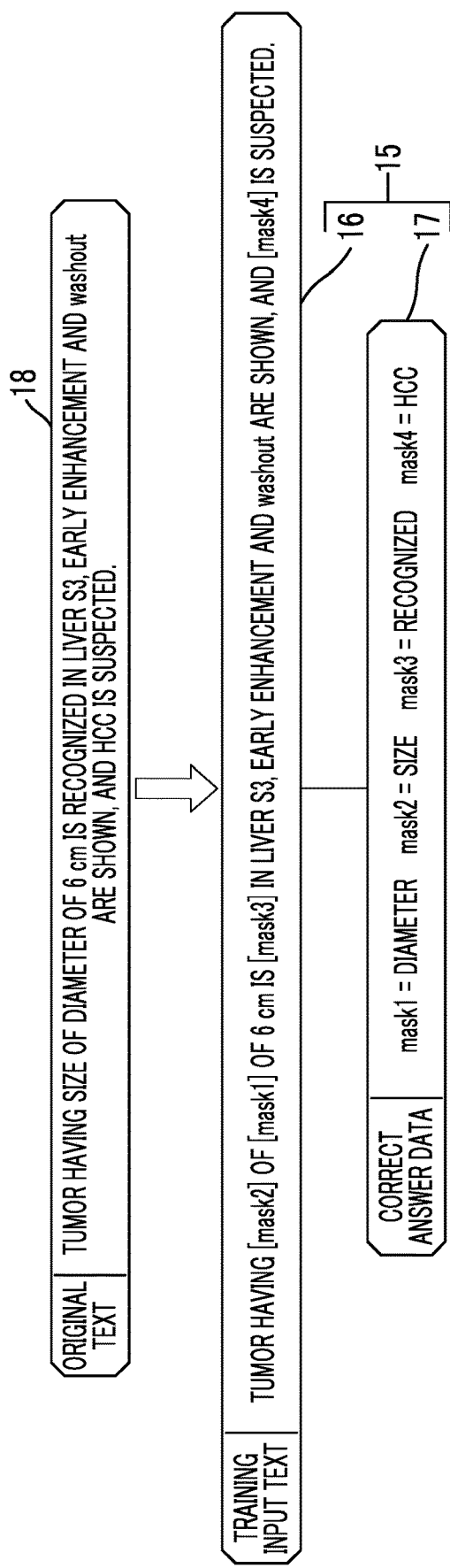
FIG. 2 is a diagram illustrating a training input text and correct answer data created from an original text of a medical document.

As illustrated in FIG. 2 as an example, the training input text 16 is a text in which a part of term phrases of an original text 18 included in the medical document 14 is masked. The correct answer data 17 is data indicating what the masked term phrase is. In FIG. 2, the original text 18 of "Tumor having a size of a diameter of 6 cm is recognized in a liver S3, early enhancement and washout are shown, and HCC is suspected." is illustrated. The training input text 16 in which four term phrases "diameter", "size", "recognized", and "HCC" (mask1 to mask 4) are masked, and the correct answer data 17 indicating each term phrase of mask1 to mask 4 are illustrated.

The training apparatus 12 receives the training data group 15G from the training data creation apparatus 11. The training apparatus 12 creates a task-adaptive model 20 from the natural language processing model 10 by training the natural language processing model 10 using the training data group 15G.

Figure 3:
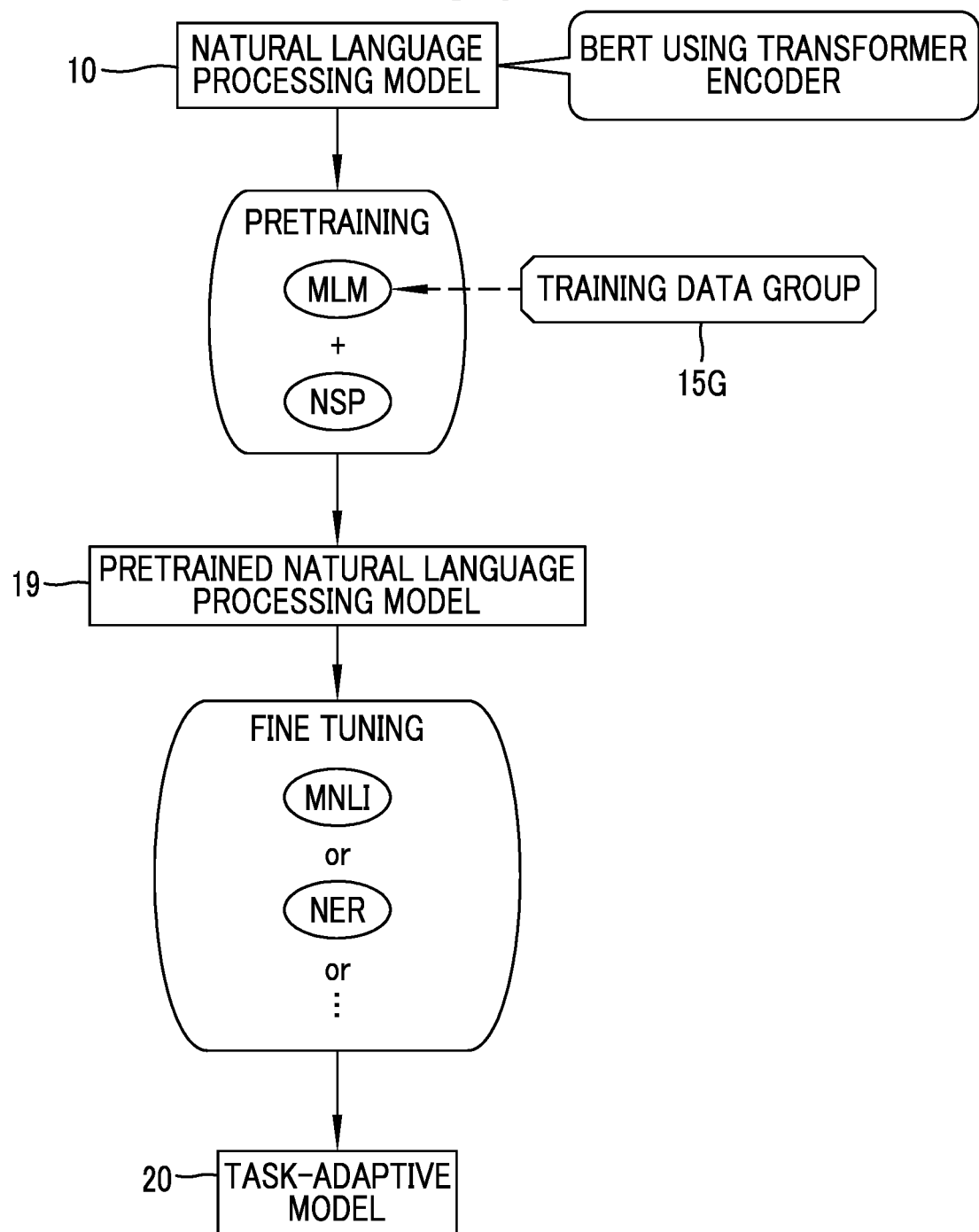
FIG. 3 is a diagram illustrating a training procedure of a natural language processing model.

More specifically, as illustrated in FIG. 3 as an example, the training apparatus 12 performs training in two stages of pretraining and fine tuning. In the pretraining, MLM and next sentence prediction (NSP) using the training data group 15G are performed. MLM is a task of causing the natural language processing model 10 to predict which term phrase fits in the masked part of the training input text 16. NSP is a task of causing the natural language processing model 10 to determine whether or not, for a training input text prepared separately from the training input text 16, two training input texts are continuous texts. In the disclosed technology, MLM is the main part, and thus, NSP will not be described in detail.

The natural language processing model 10 is changed to a pretrained natural language processing model 19 by the pretraining. The fine tuning is performed on the pretrained natural language processing model 19. The pretrained natural language processing model 19 is changed to the task-adaptive model 20 by the fine tuning. The task-adaptive model 20 is distributed to an operation apparatus, not illustrated, from the training apparatus 12.

The fine tuning is training of adjusting values of various parameters of the pretrained natural language processing model 19 set in the pretraining to values adapted to a desired natural language processing task. In the fine tuning, the medical document 14 in which a class related to the desired natural language processing task is labeled is prepared as the training data.

Examples of the natural language processing task include a task (multi-genre natural language inference (MNLI)) of determining whether two input texts are semantically implicative, contradictory, or neutral, and unique expression extraction (named entity recognition (NER)). In addition, besides these examples, examples of the natural language processing task include a task (quora question pairs (QQP)) of classifying whether or not question contents are the same, and a task (semantic textual similarity benchmark (STS-B)) of evaluating a similarity between two texts. As in the case of NSP, since MLM is the main part in the disclosed technology, the fine tuning will not be described in detail.

Figure 4:
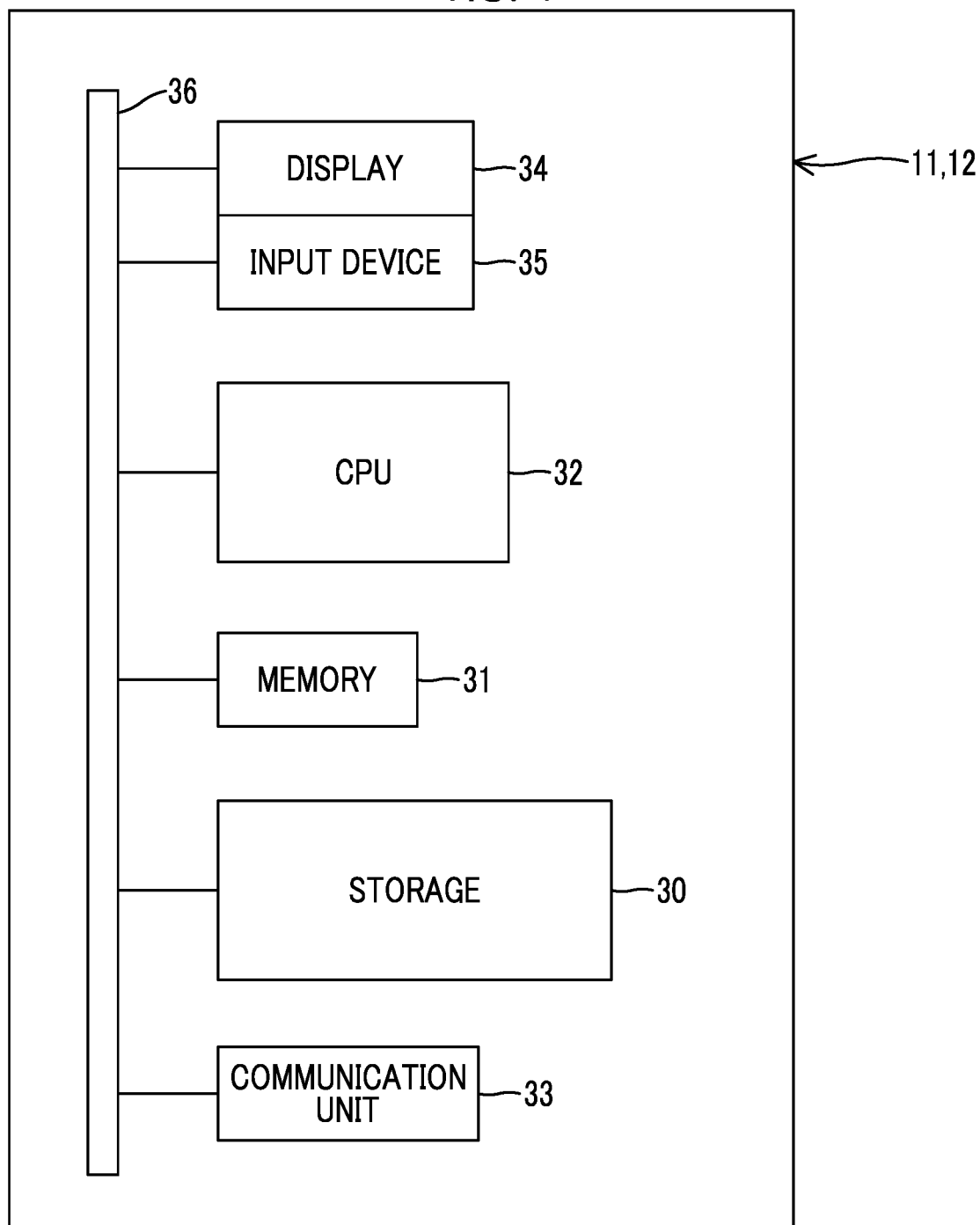
FIG. 4 is a block diagram illustrating computers constituting the training data creation apparatus and the training apparatus.

As illustrated in FIG. 4 as an example, the computers constituting the training data creation apparatus 11 and the training apparatus 12 have the same basic configuration and each comprises a storage 30, a memory 31, a central processing unit (CPU) 32, a communication unit 33, a display 34, and an input device 35. These units are connected to each other through a busline 36.

The storage 30 is a hard disk drive that is incorporated in the computers constituting the training data creation apparatus 11 and the training apparatus 12 or is connected to the computers through a cable or a network. Alternatively, the storage 30 is a disk array in which a plurality of hard disk drives are connected. The storage 30 stores a control program such as an operating system, various application programs, and various data and the like pertaining to the programs. A solid state drive may be used instead of the hard disk drive.

The memory 31 is a work memory for executing processing by the CPU 32. The CPU 32 loads the programs stored in the storage 30 into the memory 31 and executes processing corresponding to the programs. Accordingly, the CPU 32 controls each unit of the computers. The CPU 32 is an example of a "processor" according to the embodiment of the disclosed technology. The memory 31 may be incorporated in the CPU 32.

The communication unit 33 controls transmission of various information to an external apparatus. The display 34 displays various screens. An operation function based on a graphical user interface (GUI) is comprised on the various screens. The computers constituting the training data creation apparatus 11 and the training apparatus 12 receive an input of an operation instruction from the input device 35 through the various screens. The input device 35 is a keyboard, a mouse, a touch panel, a microphone for voice input, or the like. In the following description, a suffix "X" and a suffix "Y" will be attached to a reference numeral of each unit of the training data creation apparatus 11 and a reference numeral of each unit of the training apparatus 12, respectively, for distinction.

Figure 5:
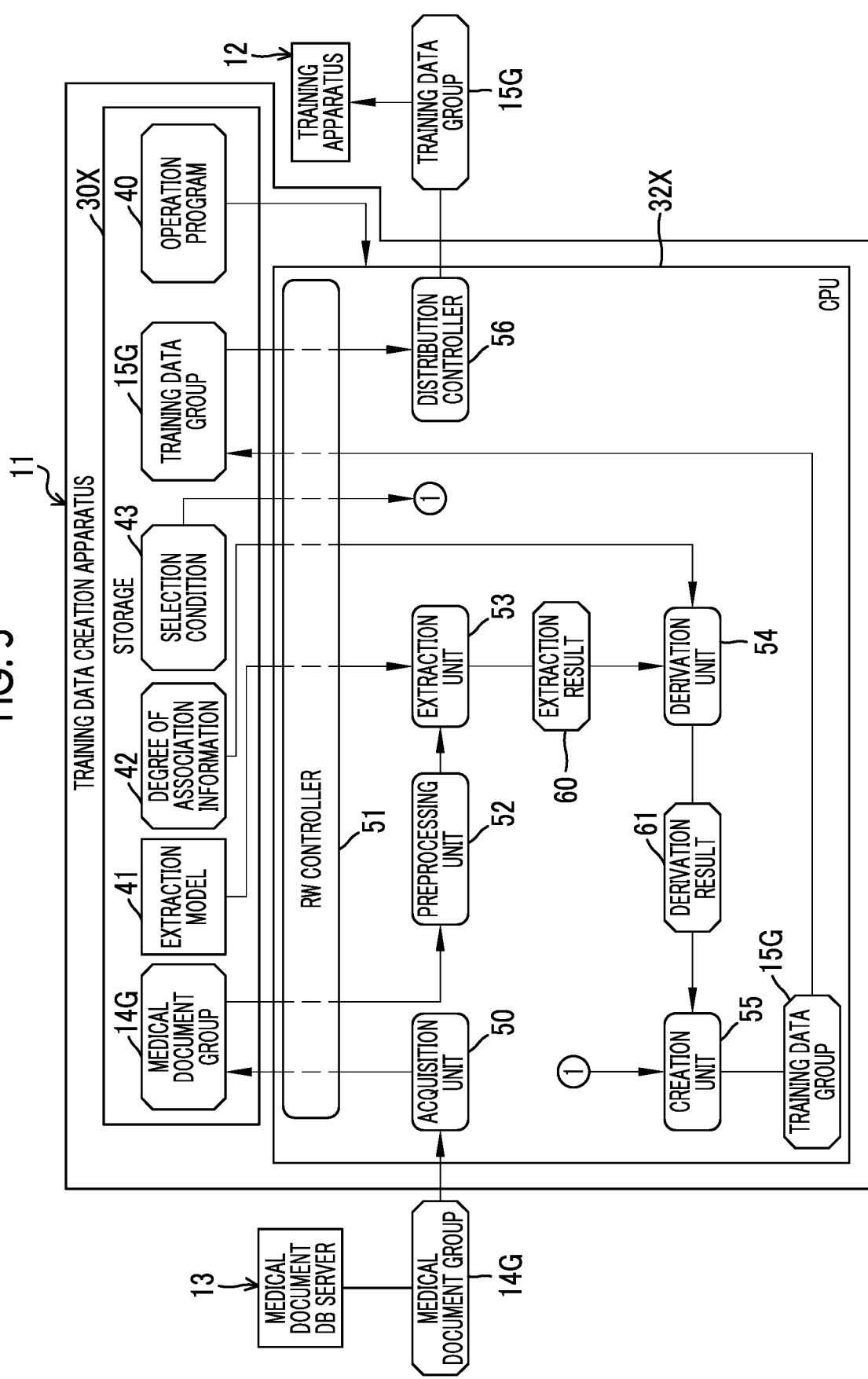
FIG. 5 is a block diagram illustrating a processing unit of a CPU of the training data creation apparatus.

As illustrated in FIG. 5 as an example, the storage 30X of the training data creation apparatus 11 stores an operation program 40. The operation program 40 is an application program causing the computer to function as the training data creation apparatus 11. That is, the operation program 40 is an example of an "operation program of an information processing apparatus" according to the embodiment of the disclosed technology. The storage 30X also stores the medical document group 14G and the training data group 15G In addition, the storage 30X also stores an extraction model 41, degree-of-association information 42, and a selection condition 43.

In a case where the operation program 40 is started, the CPU 32X of the computer constituting the training data creation apparatus 11 functions as an acquisition unit 50, a read write (hereinafter, abbreviated to RW) controller 51, a preprocessing unit 52, an extraction unit 53, a derivation unit 54, a creation unit 55, and a distribution controller 56 in cooperation with the memory 31 and the like.

The acquisition unit 50 acquires the medical document group 14G from the medical document DB server 13. The acquisition unit 50 outputs the medical document group 14G to the RW controller 51.

The RW controller 51 controls storage of various data in the storage 30X and readout of various data in the storage 30X. For example, the RW controller 51 stores the medical document group 14G from the acquisition unit 50 in the storage 30X. In addition, the RW controller 51 reads out the medical document group 14G from the storage 30X and outputs the medical document group 14G to the preprocessing unit 52.

The RW controller 51 reads out the extraction model 41 from the storage 30X and outputs the extraction model 41 to the extraction unit 53. In addition, the RW controller 51 reads out the degree-of-association information 42 from the storage 30X and outputs the degree-of-association information 42 to the derivation unit 54. Furthermore, the RW controller 51 reads out the selection condition 43 from the storage 30X and outputs the selection condition 43 to the creation unit 55.

The preprocessing unit 52 performs preprocessing on each text of each medical document 14 constituting the medical document group 14G. The preprocessing is processing of converting a text into data that can be handled in the extraction model 41.

The extraction unit 53 extracts a plurality of unique expressions from the medical document 14 using the extraction model 41. The extraction model 41 is a model created by performing the fine tuning adapted to NER on an existing pretrained natural language processing model that is different from the pretrained natural language processing model 19 and is created using a typical method of randomly selecting a target term phrase regardless of a degree of association. The extraction unit 53 outputs an extraction result 60 of the unique expression to the derivation unit 54. The unique expression is an example of a "specific term phrase" according to the embodiment of the disclosed technology.

Here, the "unique expression (named entity (NE))" is generally a collective term related to a proper noun such as a person name or a place name, a date expression, a time expression, or the like. The "unique expression" in the present example is a unique term phrase used in the medical document 14 and is more specifically a term phrase representing an anatomical site, a quantity, a lesion name, a property of a lesion, and a disease name (refer to FIG. 7).

The derivation unit 54 derives the degree of association indicating a degree of association among the plurality of unique expressions extracted by the extraction unit 53, using the degree-of-association information 42. The derivation unit 54 outputs a derivation result 61 of the degree of association to the creation unit 55.

Based on the degree of association, the creation unit 55 selects the target term phrase that is a term phrase as a target to be masked, by satisfying the selection condition 43 and creates the training input text 16 and the correct answer data 17, that is, the training data 15. The creation unit 55 creates a plurality of pieces of the training data 15. The creation unit 55 outputs the training data group 15G that is a collection of the plurality of pieces of the training data 15 to the RW controller 51. The RW controller 51 stores the training data group 15G in the storage 30X.

The RW controller 51 reads out the training data group 15G from the storage 30X and outputs the training data group 15G to the distribution controller 56. The distribution controller 56 performs a control of distributing the training data group 15G to the training apparatus 12.

Figure 6:
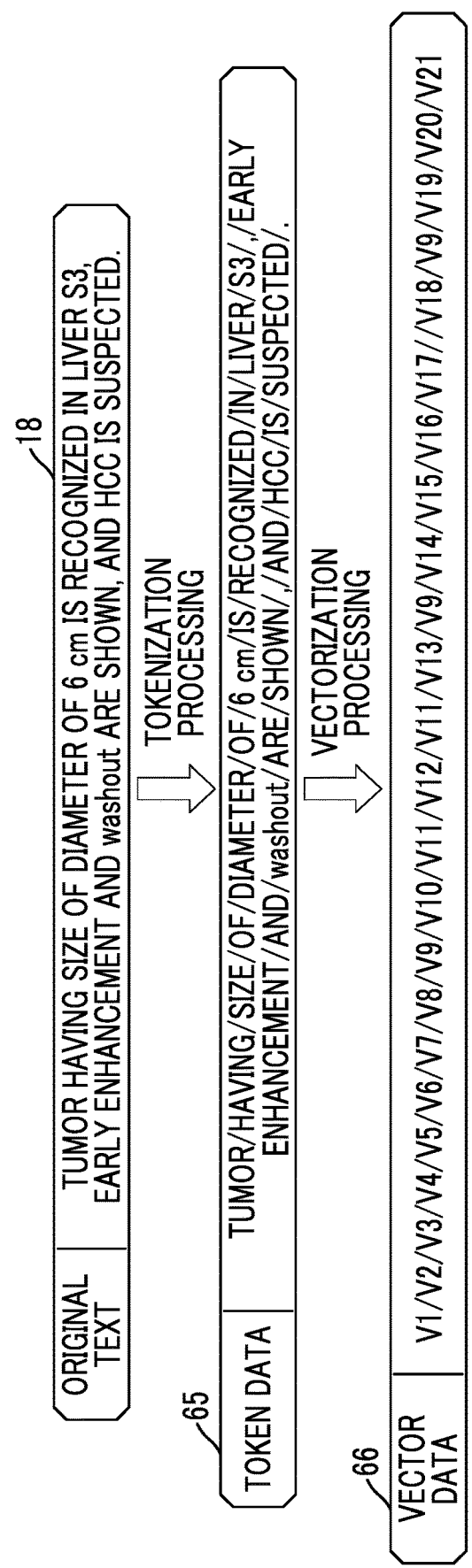
FIG. 6 is a diagram illustrating processing of a preprocessing unit.

As illustrated in FIG. 6 as an example, the preprocessing performed on each text of the medical document 14 by the preprocessing unit 52 includes tokenization processing and vectorization processing. The tokenization processing is processing of creating token data 65 by dividing the original text 18 included in the medical document 14 into tokens such as "liver", "recognized", "early enhancement", ",", and "is". In FIG. 6, morphemes (including punctuation marks) are illustrated as the tokens. Each token divided by the tokenization processing is a candidate of the target term phrase selected in the creation unit 55.

The vectorization processing is processing of creating vector data 66 by converting each token of the token data 65 into vectors V1, V2, V3, . . . of multiple dimensions, for example, 64 dimensions. The preprocessing unit 52 outputs the vector data 66 to the extraction unit 53 as the "data that can be handled in the extraction model 41".

Figure 7:
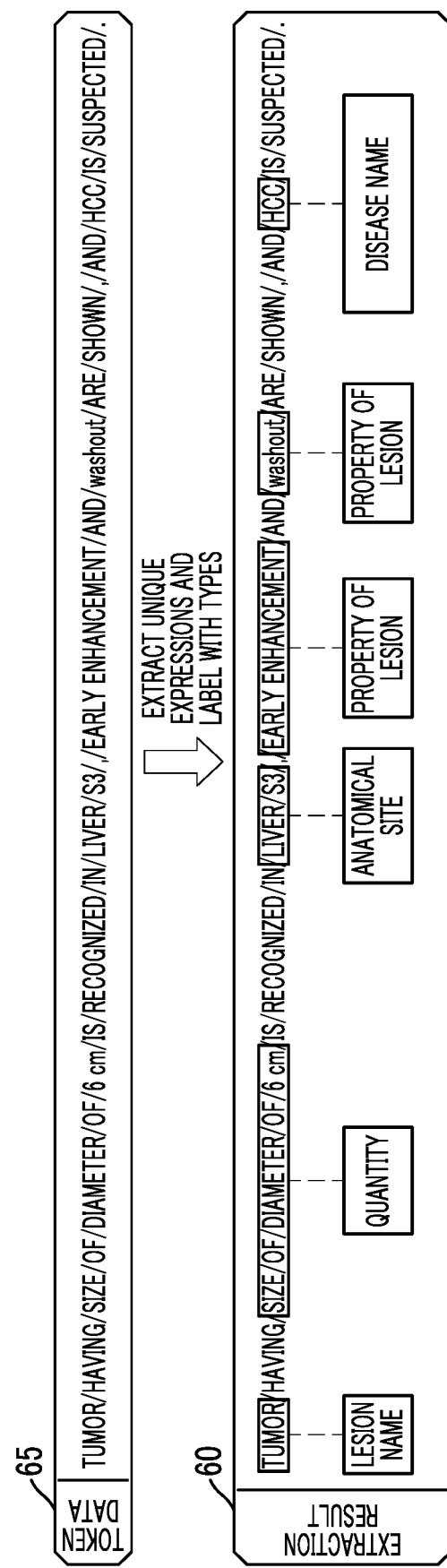
FIG. 7 is a diagram illustrating processing of an extraction unit.

As illustrated in FIG. 7 as an example, the extraction unit 53 extracts term phrases representing the anatomical site, the quantity, the lesion name, the property of the lesion, and the disease name from the medical document 14 as the unique expressions using the extraction model 41. In addition, the extraction unit 53 labels types of the extracted unique expressions. The types of the unique expressions are the anatomical site, the quantity, the lesion name, the property of the lesion, and the disease name. In FIG. 7, an example in which "liver/S3", "diameter/6 cm/size", "tumor", "early enhancement", "washout", and "HCC" are extracted as the unique expressions is illustrated. An example of labeling "liver/S3" with the anatomical site, labeling "diameter/6 cm/size" with the quantity, labeling "tumor" with the lesion name, labeling "early enhancement" and "washout" with the property of the lesion, and labeling "HCC" with the disease name is illustrated. While the extraction model 41 handles the vector data 66, the token data 65 is illustrated in FIG. 7 for convenience of description.

As illustrated in FIG. 8 as an example, the degree of association is registered in the degree-of-association information 42 for each combination of two types of the unique expressions. The degree of association is set in advance by an operator of the training data creation apparatus 11 based on knowledge and experience acquired so far. For example, a highest value of 10 is set for a combination "property of lesion-disease name" as the degree of association. On the other hand, a lowest value of 0 is set for a combination "quantity-property of lesion" as the degree of association.

As illustrated in FIG. 9 as an example, the degree of association derived using the degree-of-association information 42 is registered in the derivation result 61 for each combination of two unique expressions. In FIG. 9, the derivation result 61 of the text illustrated in FIG. 7 is illustrated. For example, a degree of association 8 is registered for a combination "liver S3-tumor" that is a combination "anatomical site-lesion name". In addition, a degree of association 10 is registered for combinations "early enhancement-HCC" and "washout-HCC" that are the combination "property of lesion-disease name".

As illustrated in FIG. 10 as an example, the selection condition 43 includes the following three conditions. A content of a first condition is that 15% of tokens of one text are masked. As in the example illustrated in FIG. 7, in a case where the number of tokens of one text is 25, 25×0.15=3.75 is satisfied. Thus, in a case where at least four tokens are masked, the first condition is satisfied. A content of a second condition is that at least one unique expression is selected as the target term phrase. In the example illustrated in FIG. 7, in a case where at least any one of "liver/S3", "diameter/6 cm/size", "tumor", "early enhancement", "washout", or "HCC" is selected as the target term phrase, the second condition is satisfied. A content of a third condition is that at least one unique expression of which the degree of association with the term phrase selected as the target term phrase is greater than or equal to 8 is excluded from the candidates of the target term phrase. In the third condition, "degree of association is greater than or equal to 8" is an example of a "condition set in advance" according to the embodiment of the disclosed technology.

Figure 11:
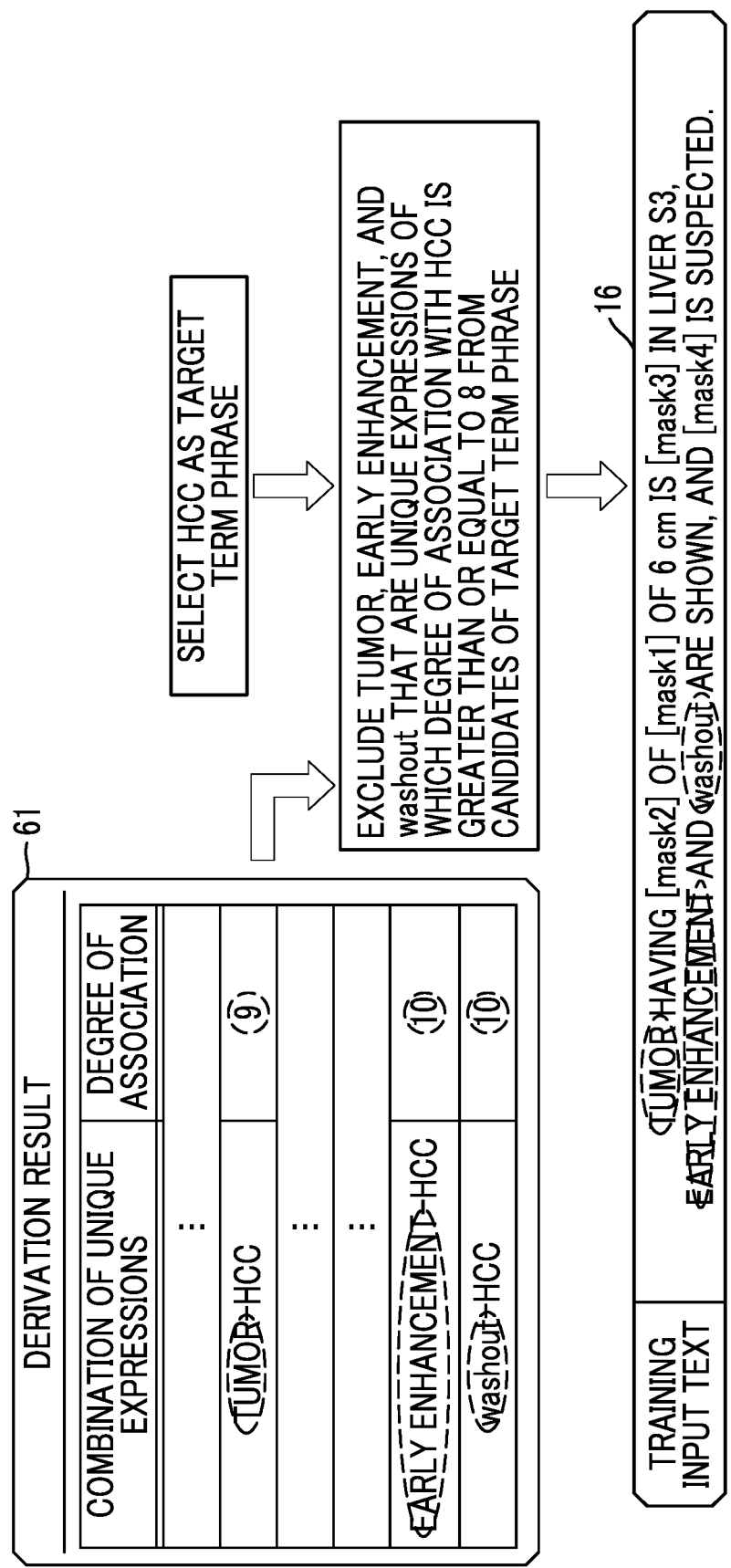
FIG. 11 is a diagram illustrating processing of a creation unit.

FIG. 11 illustrates a case where "HCC" that is the unique expression is selected as the target term phrase in the example illustrated in FIG. 7. In this case, according to the derivation result 61, "tumor", "early enhancement", and "washout" are unique expressions of which the degree of association with "HCC" is greater than or equal to 8. Thus, the creation unit 55 excludes "tumor", "early enhancement", and "washout" from the candidates of the target term phrase in accordance with the third condition. In other words, the creation unit 55 does not select "tumor", "early enhancement", and "washout" as the target term phrase and leaves "tumor", "early enhancement", and "washout" in the training input text 16. On the other hand, the creation unit 55 does not exclude "liver/S3" and "diameter/6 cm/size" that are unique expressions of which the degree of association with "HCC" is less than 8 from the candidates of the target term phrase. Thus, in FIG. 11, each of "diameter" and "size" in "diameter/6 cm/size" is selected as the target term phrase. Here, "HCC" is an example of a "target term phrase" and a "term phrase selected as a target term phrase" according to the embodiment of the disclosed technology.

Figure 12:
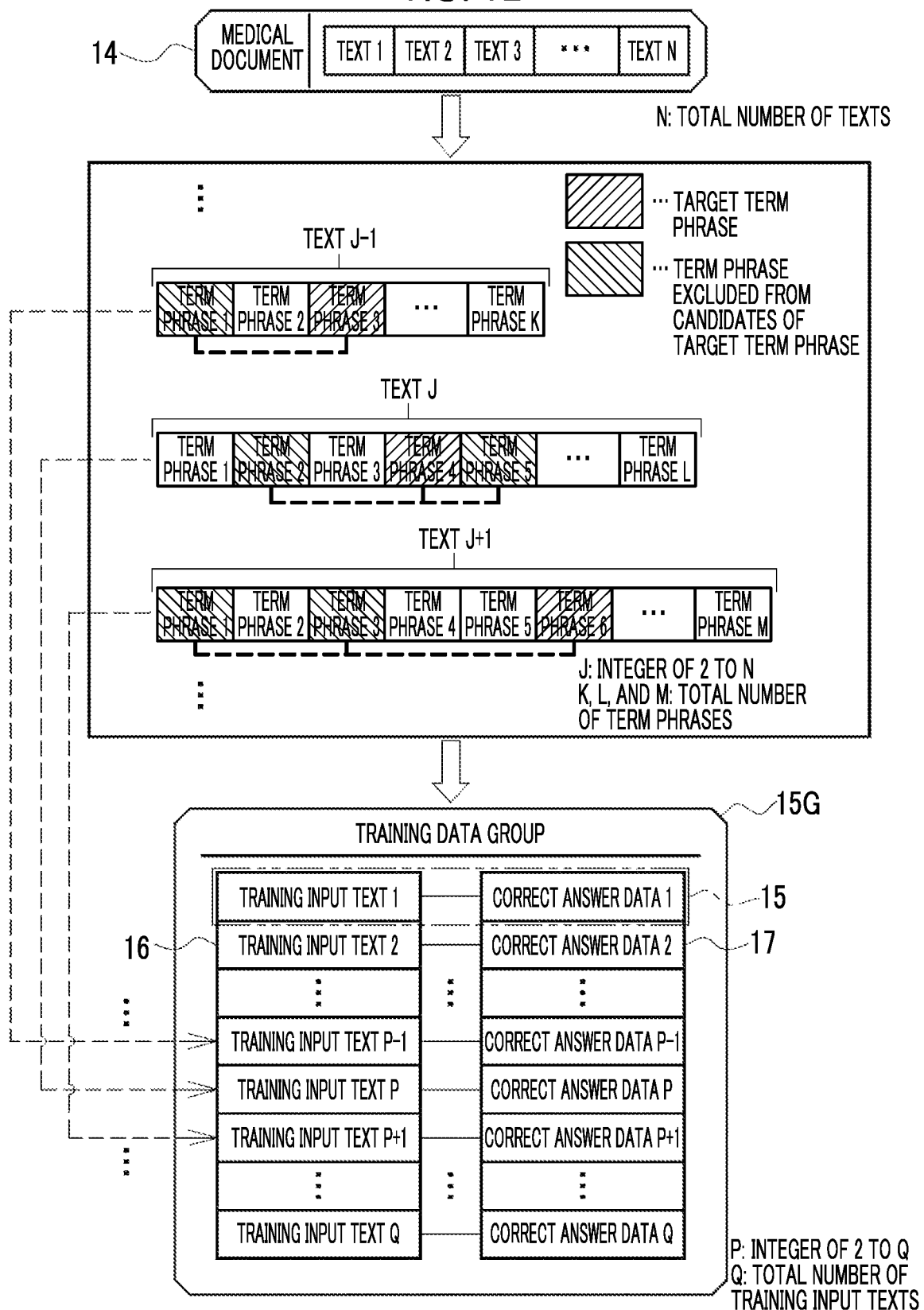
FIG. 12 is a diagram of overall processing of the training data creation apparatus.

FIG. 12 is a diagram of overall processing of the training data creation apparatus 11. In the training data creation apparatus 11, first, the unique expressions of each text of the medical document 14 are extracted in the extraction unit 53. The degree of association among the unique expressions is derived in the derivation unit 54. Last, the target term phrase is selected in the creation unit 55 based on the degree of association. Specifically, at least one unique expression of which the degree of association with the term phrase selected as the target term phrase is greater than or equal to 8 is excluded from the candidates of the target term phrase. By doing so, the training input text 16 and the correct answer data 17, that is, the training data 15, are created. In FIG. 12, an example of creating a training input text P−1 and correct answer data P−1, a training input text P and correct answer data P, and a training input text P+1 and correct answer data P+1 (P is an integer of 2 to Q and Q is the total number of the training input texts 16) from, among N texts of a text 1 to a text N of the medical document 14, a text J−1, a text J, and a text J+1 (J is an integer of 2 to N), respectively, is illustrated. The training input texts 16 also include a certain number of training input texts created using the typical method of randomly selecting the target term phrase regardless of the degree of association.

Figure 13:
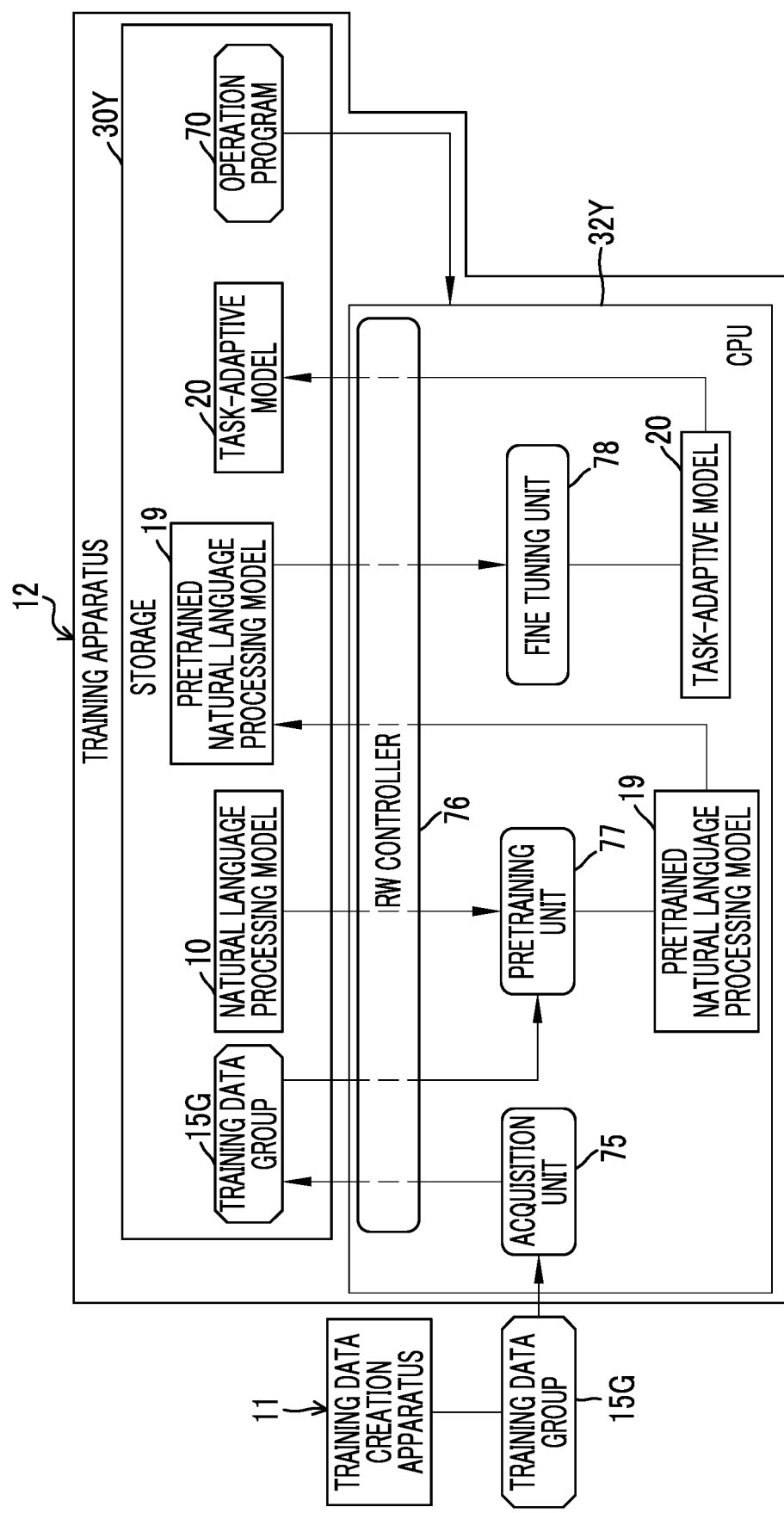
FIG. 13 is a block diagram illustrating a processing unit of a CPU of the training apparatus.

As illustrated in FIG. 13 as an example, the storage 30Y of the training apparatus 12 stores an operation program 70. The operation program 70 is an application program causing the computer to function as the training apparatus 12. That is, as in the case of the operation program 40, the operation program 70 is an example of an "operation program of an information processing apparatus" according to the embodiment of the disclosed technology. The storage 30Y also stores the natural language processing model 10 and the like.

In a case where the operation program 70 is started, the CPU 32Y of the computer constituting the training apparatus 12 functions as an acquisition unit 75, a RW controller 76, a pretraining unit 77, and a fine tuning unit 78 in cooperation with the memory 31 and the like.

The acquisition unit 75 acquires the training data group 15G from the training data creation apparatus 11. The acquisition unit 75 outputs the training data group 15G to the RW controller 76.

The RW controller 76 controls storage of various data in the storage 30Y and readout of various data in the storage 30Y. For example, the RW controller 76 stores the training data group 15G from the acquisition unit 75 in the storage 30Y. In addition, the RW controller 76 reads out the training data group 15G from the storage 30Y and outputs the training data group 15G to the pretraining unit 77. Furthermore, the RW controller 76 reads out the natural language processing model 10 from the storage 30Y and outputs the natural language processing model 10 to the pretraining unit 77.

The pretraining unit 77 changes the natural language processing model 10 to the pretrained natural language processing model 19 by performing the pretraining on the natural language processing model 10 using the training data 15. The pretraining unit 77 outputs the pretrained natural language processing model 19 to the RW controller 76. The RW controller 76 stores the pretrained natural language processing model 19 in the storage 30Y.

The RW controller 76 reads out the pretrained natural language processing model 19 from the storage 30Y and outputs the pretrained natural language processing model 19 to the fine tuning unit 78. The fine tuning unit 78 changes the pretrained natural language processing model 19 to the task-adaptive model 20 by performing the fine tuning on the pretrained natural language processing model 19. The fine tuning unit 78 outputs the task-adaptive model 20 to the RW controller 76. The RW controller 76 stores the task-adaptive model 20 in the storage 30Y.

The task-adaptive model 20 is distributed to the operation apparatus by a distribution controller, not illustrated, and is used in the operation apparatus. Alternatively, the training apparatus 12 may function as the operation apparatus, and the task-adaptive model 20 may be used in the training apparatus 12.

Figure 14:
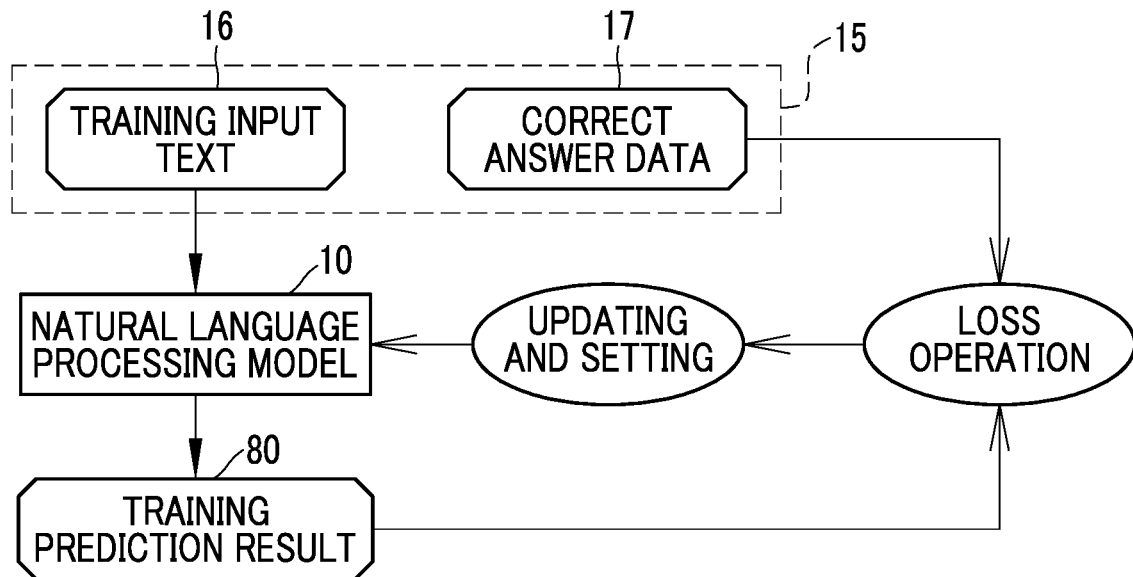
FIG. 14 is a diagram illustrating a summary of processing in MLM in pretraining of the natural language processing model.

As illustrated in FIG. 14 as an example, in the pretraining, the training input text 16 is input into the natural language processing model 10. The natural language processing model 10 outputs a training prediction result 80 with respect to the training input text 16. A loss operation of the natural language processing model 10 using a loss function is performed based on the training prediction result 80 and the correct answer data 17. Updating and setting of values of various parameters of the natural language processing model 10 are performed in accordance with a result of the loss operation, and the natural language processing model 10 is updated in accordance with the updating and the setting. The training input text 16 is converted into the vector data 66 in the natural language processing model 10. In addition, the training prediction result 80 represents a predicted term phrase of the masked term phrase using the vector data 66.

In the pretraining, the series of processing of the input of the training input text 16 into the natural language processing model 10, the output of the training prediction result 80 from the natural language processing model 10, the loss operation, the updating and the setting, and the updating of the natural language processing model 10 are repeated while the training data 15 is exchanged. The repetition of the series of processing is finished in a case where prediction accuracy of the training prediction result 80 with respect to the correct answer data 17 has reached a predetermined set level. The natural language processing model 10 for which the prediction accuracy has reached the set level is handled as the pretrained natural language processing model 19. The pretraining may be finished in a case where the series of processing is repeated a set number of times, regardless of the prediction accuracy of the training prediction result 80 with respect to the correct answer data 17.

Figure 15:
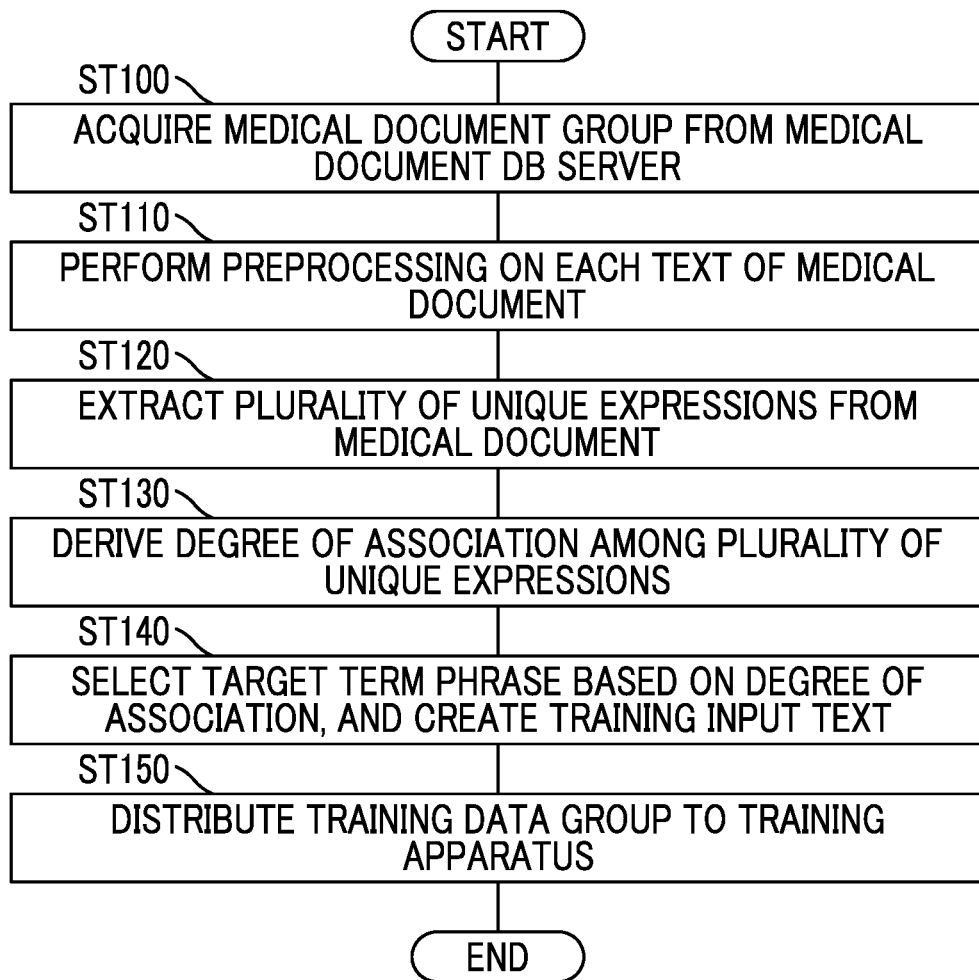
FIG. 15 is a flowchart illustrating a processing procedure of the training data creation apparatus.
Figure 16:
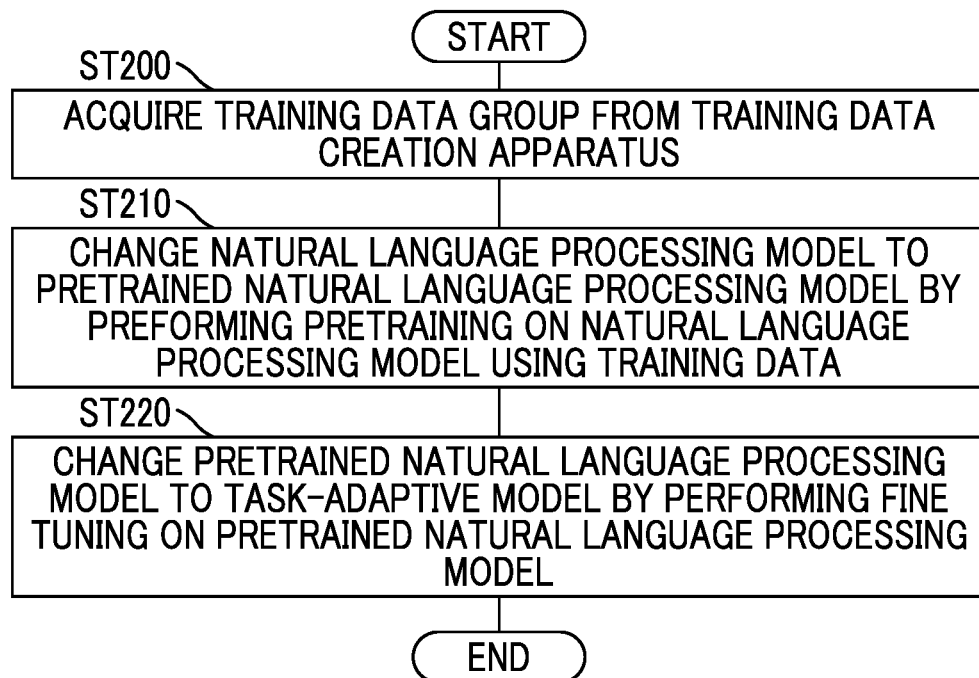
FIG. 16 is a flowchart illustrating a processing procedure of the training apparatus.

Next, an action of the above configuration will be described with reference to the flowcharts illustrated in FIG. 15 and FIG. 16 as an example. First, in a case where the operation program 40 is started in the training data creation apparatus 11, the CPU 32X of the training data creation apparatus 11 functions as the acquisition unit 50, the RW controller 51, the preprocessing unit 52, the extraction unit 53, the derivation unit 54, the creation unit 55, and the distribution controller 56 as illustrated in FIG. 5.

The operator of the training data creation apparatus 11 transmits a distribution request of the medical document group 14G to the medical document DB server 13. As illustrated in FIG. 15, the medical document group 14G distributed from the medical document DB server 13 in accordance with the distribution request is acquired in the acquisition unit 50 (step ST100). The medical document group 14G is output to the RW controller 51 from the acquisition unit 50 and is stored in the storage 30X under control of the RW controller 51.

The medical document group 14G is read out from the storage 30X by the RW controller 51. The medical document group 14G is output to the preprocessing unit 52 from the RW controller 51. As illustrated in FIG. 6, the preprocessing including the tokenization processing and the vectorization processing is performed on each text of the medical document 14 in the preprocessing unit 52 (step ST110).

Next, as illustrated in FIG. 7, a plurality of the unique expressions are extracted from the medical document 14 by the extraction unit 53 using the extraction model 41 (step ST120). The extraction result 60 of the unique expressions is output to the derivation unit 54 from the extraction unit 53.

In the derivation unit 54, the degree of association among the plurality of unique expressions is derived as in the derivation result 61 illustrated in FIG. 9 using the degree-of-association information 42 illustrated in FIG. 8 (step ST130). The derivation result 61 is output to the creation unit 55 from the derivation unit 54.

In the creation unit 55, the target term phrase is selected as illustrated in FIG. 11 based on the degree of association by satisfying the selection condition 43 illustrated in FIG. 10, and the training input text 16 and the training data 15 are created (step ST140). More specifically, 15% of the tokens of one text are masked, and at least one unique expression is selected as the target term phrase. In addition, the unique expression of which the degree of association with the term phrase selected as the target term phrase is greater than or equal to 8 is excluded from the candidates of the target term phrase. The training data group 15G is output to the RW controller 51 from the creation unit 55 and is stored in the storage 30X under control of the RW controller 51.

The training data group 15G is read out from the storage 30X by the RW controller 51. The training data group 15G is output to the distribution controller 56 from the RW controller 51. The training data group 15G is distributed to the training apparatus 12 under control of the distribution controller 56 (step ST150).

In a case where the operation program 70 is started in the training apparatus 12, the CPU 32Y of the training apparatus 12 functions as the acquisition unit 75, the RW controller 76, the pretraining unit 77, and the fine tuning unit 78 as illustrated in FIG. 13.

An operator of the training apparatus 12 transmits a distribution request of the training data group 15G to the training data creation apparatus 11. As illustrated in FIG. 16, the training data group 15G distributed from the training data creation apparatus 11 in accordance with the distribution request is acquired in the acquisition unit 75 (step ST200). The training data group 15G is output to the RW controller 76 from the acquisition unit 75 and is stored in the storage 30Y under control of the RW controller 76.

The training data group 15G and the natural language processing model 10 are read out from the storage 30Y by the RW controller 76. The training data group 15G and the natural language processing model 10 are output to the pretraining unit 77 from the RW controller 76. As illustrated in FIG. 14, in the pretraining unit 77, the pretraining is performed on the natural language processing model 10 using the training data 15. Accordingly, the natural language processing model 10 is changed to the pretrained natural language processing model 19 (step ST210). The pretrained natural language processing model 19 is output to the RW controller 76 from the pretraining unit 77 and is stored in the storage 30Y under control of the RW controller 76.

The pretrained natural language processing model 19 is read out from the storage 30Y by the RW controller 76. The pretrained natural language processing model 19 is output to the fine tuning unit 78 from the RW controller 76. In the fine tuning unit 78, the fine tuning is performed on the pretrained natural language processing model 19. Accordingly, the pretrained natural language processing model 19 is changed to the task-adaptive model 20 (step ST220). The task-adaptive model 20 is output to the RW controller 76 from the fine tuning unit 78 and is stored in the storage 30Y under control of the RW controller 76.

As described above, the CPU 32X of the training data creation apparatus 11 comprises the extraction unit 53, the derivation unit 54, and the creation unit 55. The extraction unit 53 extracts the plurality of unique expressions that are specific term phrases from the medical document 14. The derivation unit 54 derives the degree of association indicating the degree of association among the plurality of unique expressions. Based on the degree of association, the creation unit 55 selects the target term phrase that is the term phrase as a target to be masked. Thus, the training input text 16 that contributes to effective training of the natural language processing model 10 can be created, compared to the typical method of randomly selecting the target term phrase regardless of the degree of association and the method of Chen Lin, et al: EntityBERT: Entity-centric Masking Strategy for Model Pretraining for the Clinical Domain, Proceedings of the BioNLP 2021 workshop, pages 191-201 Jun. 11, 2021 in which there is a concern that a term phrase necessary for predicting the target term phrase is also masked without considering the degree of association.

The creation unit 55 excludes the unique expression of which the degree of association with the term phrase selected as the target term phrase satisfies the condition set in advance, from the candidates of the target term phrase. Thus, the unique expression necessary for predicting the term phrase selected as the target term phrase can be left in the training input text 16. Accordingly, a concern that it is difficult to predict the masked term phrase can be reduced. Consequently, it is possible to further contribute to the effective training of the natural language processing model 10.

The derivation unit 54 derives the degree of association using the degree-of-association information 42 in which the degree of association corresponding to the combination of the types of the unique expressions is set in advance. Thus, in a case where the unique expressions are extracted, and the type of each unique expression is labeled, the degree of association can be easily derived using the degree-of-association information 42. In addition, as in the present example, in a case where the operator sets the degree of association of the degree-of-association information 42, an idea of the operator can be reflected on the creation of the training input text 16.

A document is the medical document 14, and the types of the unique expressions include the anatomical site, the quantity, the lesion name, the property of the lesion, and the disease name. It is difficult to obtain a large amount of the medical document 14 that is the document as a base of the training input text. Thus, a concern that the effective pretraining is not performed by losing a training opportunity for an important term phrase is increased. Accordingly, as in the present example, in a case where the document is the medical document 14, and the types of unique expressions are the anatomical site, the quantity, the lesion name, the property of the lesion, and the disease name, an effect of being able to create the training input text 16 contributing to the effective training of the natural language processing model 10 can be further exhibited. The types of unique expressions may include at least one of the anatomical site, the quantity, the lesion name, the property of the lesion, or the disease name.

The pretraining unit 77 of the training apparatus 12 performs the pretraining on the natural language processing model 10 using the training input text 16 created in the training data creation apparatus 11 as described above. Thus, the effective training of the natural language processing model 10 can be performed.

Embodiment 2

Figure 17:
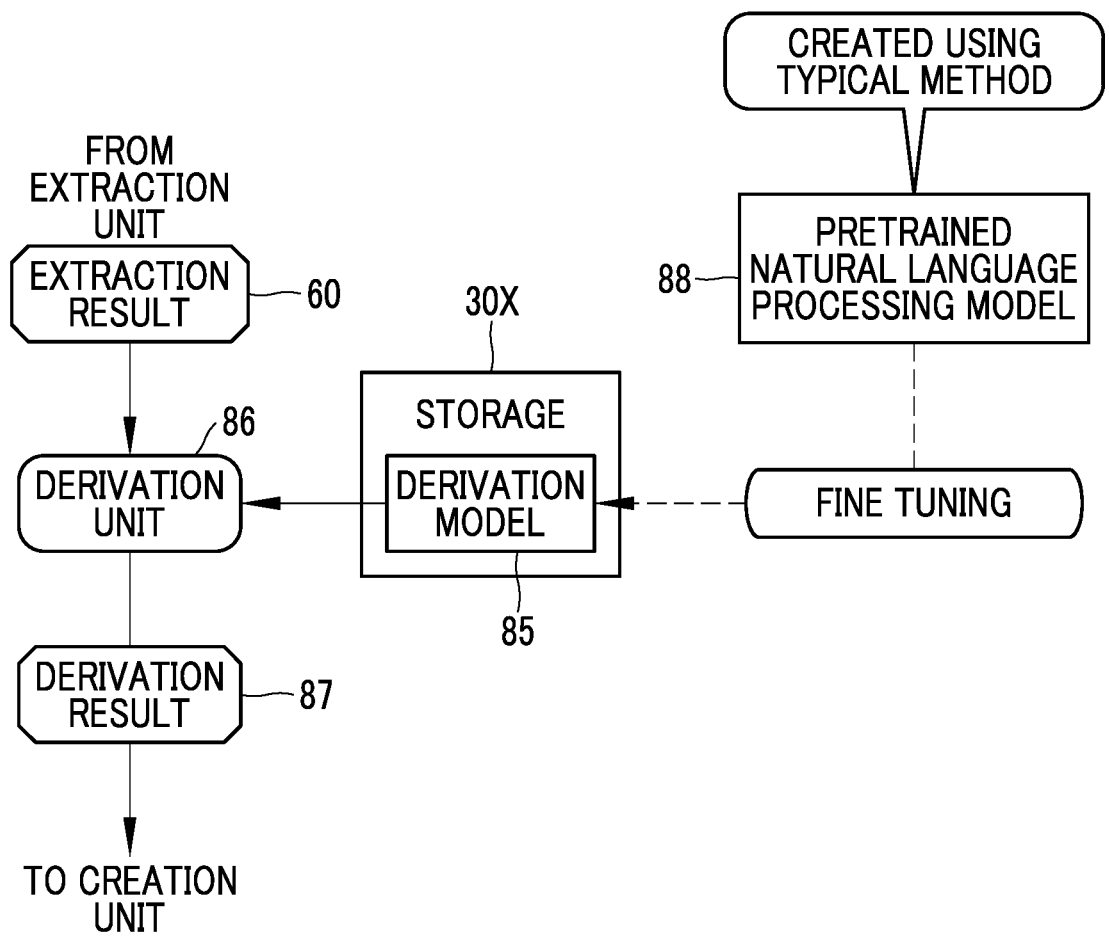
FIG. 17 is a diagram illustrating Embodiment 2 in which a degree of association is derived using a trained derivation model.

In Embodiment 1, while the degree of association is derived using the degree-of-association information 42, the disclosed technology is not limited thereto. As illustrated in FIG. 17 as an example, the degree of association may be derived using a derivation model 85.

In FIG. 17, a derivation unit 86 of Embodiment 2 derives the degree of association using the derivation model 85 and outputs a derivation result 87 to the creation unit 55. The derivation model 85 is stored in the storage 30X. The derivation model 85 is a model created by performing the fine tuning adapted to the derivation of the degree of association on a pretrained natural language processing model 88. The pretrained natural language processing model 88 is a model different from the pretrained natural language processing model 19. The pretrained natural language processing model 88 is a model created by training using the training input text 16 created using the typical method of randomly selecting the target term phrase regardless of the degree of association. The derivation model 85 is an example of a "trained derivation model" according to the embodiment of the disclosed technology. In addition, the pretrained natural language processing model 88 is an example of a "trained natural language processing model" according to the embodiment of the disclosed technology.

Figure 18:
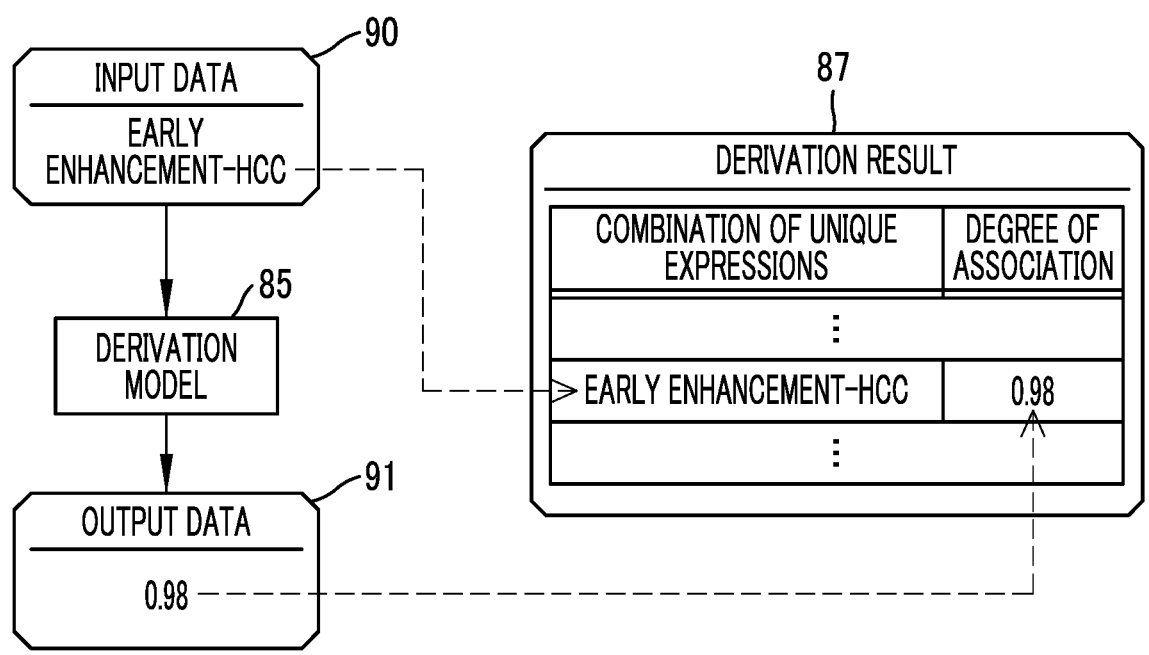
FIG. 18 is a diagram illustrating a derivation result in Embodiment 2.

As illustrated in FIG. 18 as an example, the combination of the unique expressions extracted by the extraction unit 53 is input into the derivation model 85 as input data 90. The derivation model 85 outputs output data 91 with respect to the input data 90. The output data 91 is a score representing the degree of association among the unique expressions of the input data 90 using a numerical value between 0 and 1. The derivation unit 86 registers the score of the output data 91 in the derivation result 87 as the degree of association. In FIG. 18, a case where the combination "early enhancement-HCC" is input into the derivation model 85 as the input data 90 and 0.98 is output as the output data 91 is illustrated. In this case, for example, the content of the third condition of the selection condition 43 is that at least one unique expression of which the degree of association with the term phrase selected as the target term phrase is greater than or equal to 0.8 is excluded from the candidates of the target term phrase.

In Embodiment 2, the derivation unit 86 derives the degree of association using the trained derivation model 85. Thus, the degree of association can be easily derived by the derivation model 85 as long as the unique expressions are extracted. In addition, an effort of setting the degree of association by the operator as in the degree-of-association information 42 can be reduced. In addition, the derivation model 85 is created based on the pretrained natural language processing model 88. Thus, the derivation model 85 can be simply created.

Embodiment 3

In Embodiment 3 illustrated in FIG. 19 to FIG. 25, a text of the same type as the text including the term phrase selected as the target term phrase is determined, and the text including the target term phrase and the text of the same type are used as the training input text 16.

Embodiment 3_1

Figure 19:
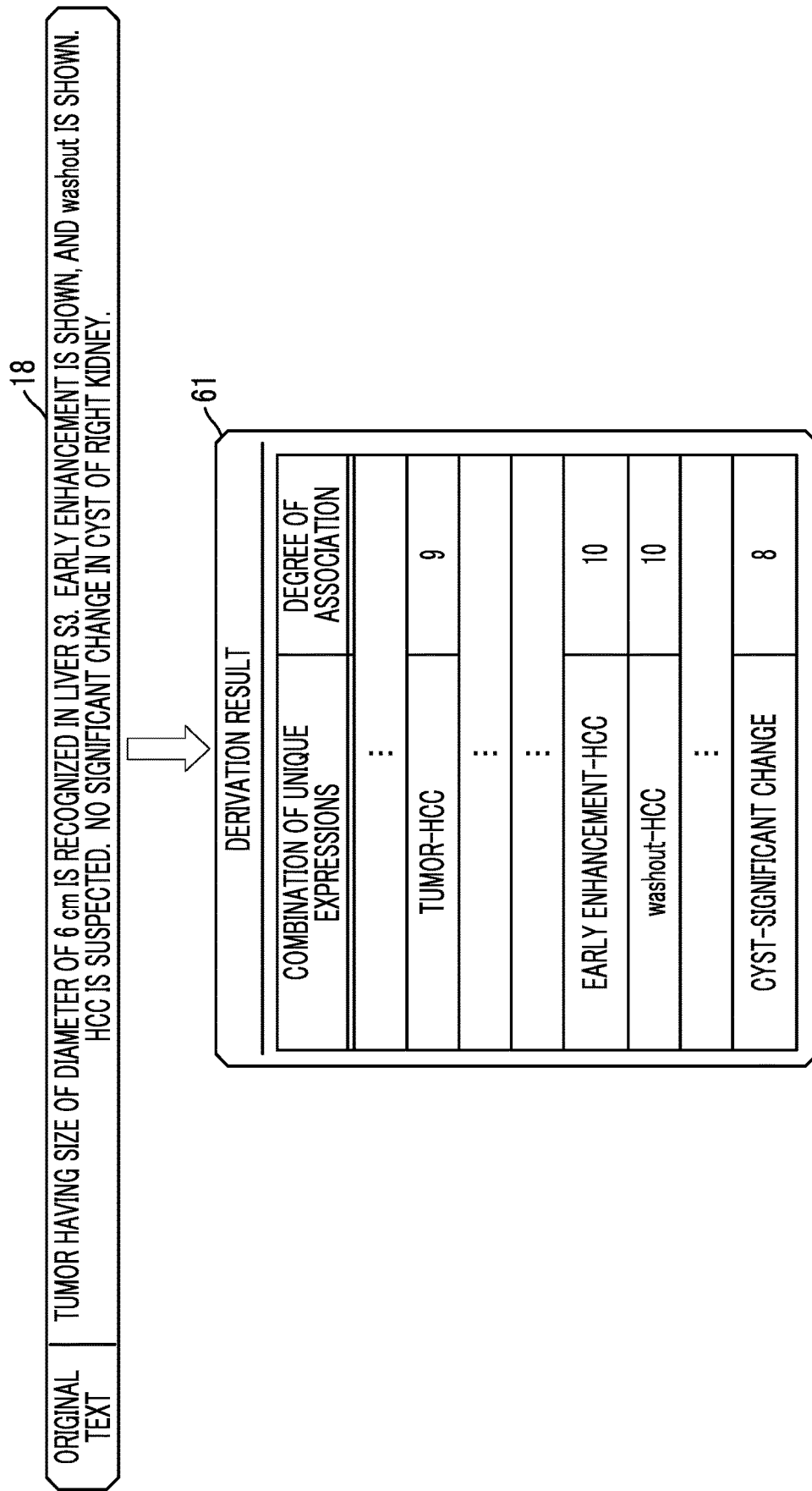
FIG. 19 is a diagram illustrating a derivation result in Embodiment 3_1.

FIG. 19 illustrates the derivation result 61 with respect to the original text 18 consisting of four texts "Tumor having a size of a diameter of 6 cm is recognized in a liver S3.", "Early enhancement is shown, and washout is shown.", "HCC is suspected.", and "No significant change in a cyst of a right kidney." In this case, unique expressions "right kidney", "cyst", and "significant change" are extracted in addition to "liver S3", "early enhancement", "HCC", and the like of Embodiment 1, and the degree of association is derived for "right kidney, "cyst", and "significant change".

Figure 20:
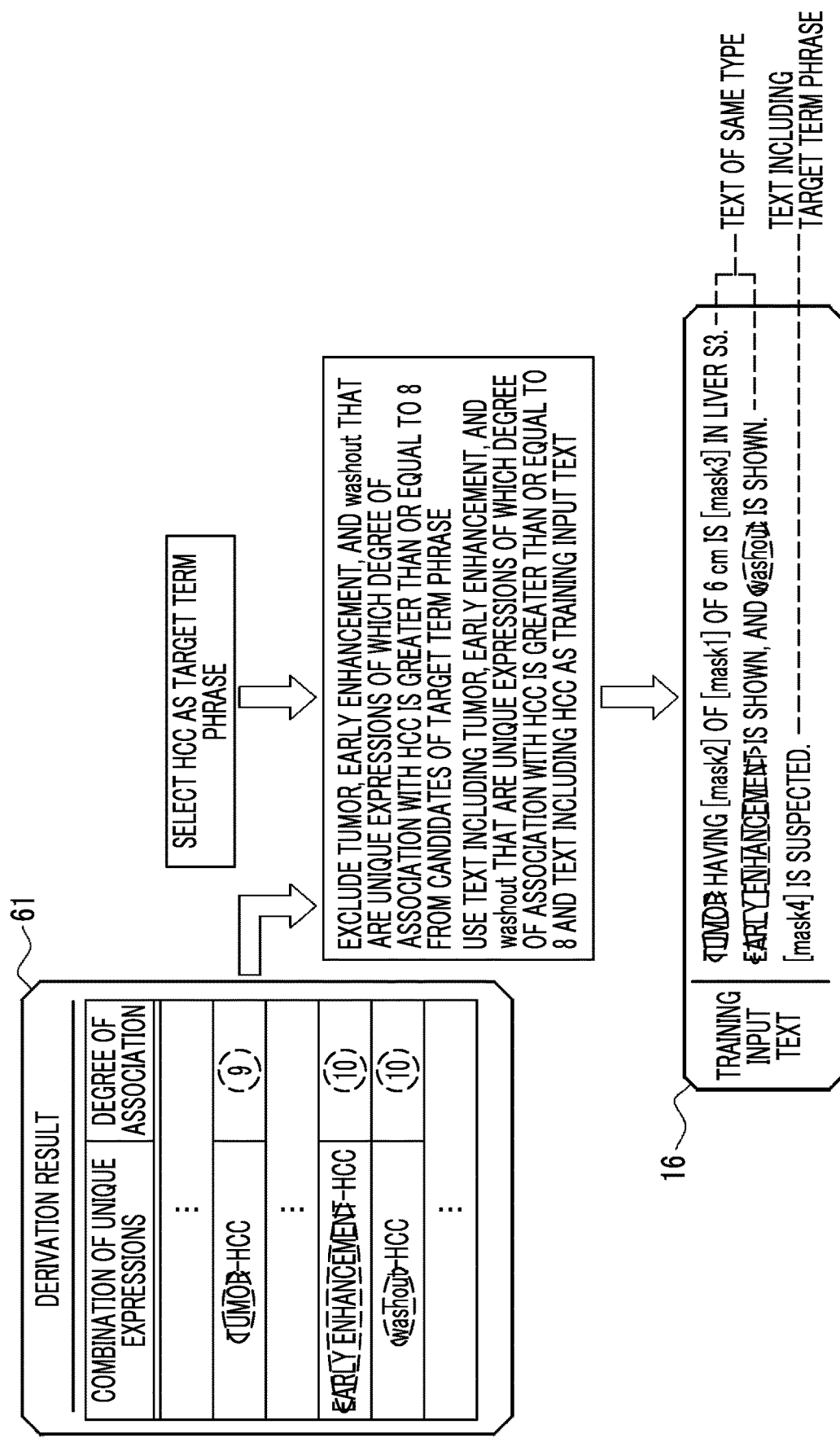
FIG. 20 is a diagram illustrating processing of a creation unit in Embodiment 3_1.

FIG. 20 illustrates a case where "HCC" that is the unique expression is selected as the target term phrase as in the example illustrated in FIG. 11. In this case, according to the derivation result 61, "tumor", "early enhancement", and "washout" are unique expressions of which the degree of association with "HCC" is greater than or equal to 8. Thus, the creation unit 55 excludes "tumor", "early enhancement", and "washout" from the candidates of the target term phrase. In addition, the creation unit 55 determines that "Tumor having a size of a diameter of 6 cm is recognized in a liver S3." and "Early enhancement is shown, and washout is shown." that are texts including "tumor", "early enhancement", and "washout" are texts of the same type as "HCC is suspected." that is a text including "HCC". The creation unit 55 uses "HCC is suspected.", "Tumor having a size of a diameter of 6 cm is recognized in a liver S3.", and "Early enhancement is shown, and washout is shown." as the training input texts 16 to be collectively input into the natural language processing model 10 at once. Here, "HCC is suspected." is an example of a "text including a term phrase selected as a target term phrase" and a "text including a target term phrase" according to the embodiment of the disclosed technology. In addition, "Tumor having a size of a diameter of 6 cm is recognized in a liver S3." and "Early enhancement is shown, and washout is shown." are an example of a "text of the same type" according to the embodiment of the disclosed technology.

Figure 21:
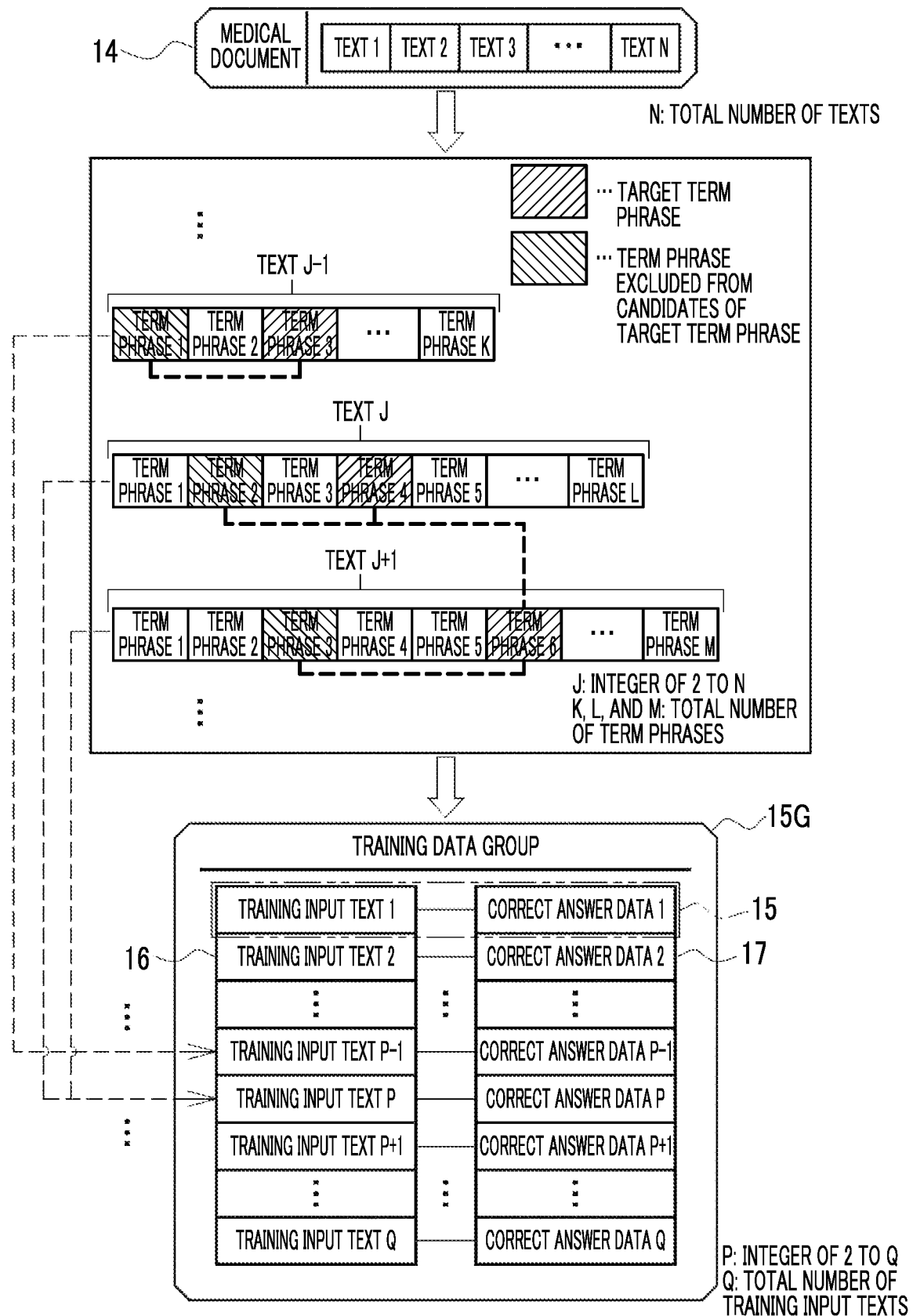
FIG. 21 is a diagram of overall processing of a training data creation apparatus in Embodiment 3_1.

FIG. 21 is a diagram of overall processing of a training data creation apparatus in Embodiment 3_1. In the training data creation apparatus of Embodiment 3_1, first, the unique expressions of each text of the medical document 14 are extracted in the extraction unit 53 as in Embodiment 1. The degree of association among the unique expressions is derived in the derivation unit 54. Last, the target term phrase is selected in the creation unit 55 based on the degree of association. Specifically, at least one unique expression of which the degree of association with the term phrase selected as the target term phrase is greater than or equal to 8 is excluded from the candidates of the target term phrase. In addition, in the creation unit 55, the text of the same type as the text including the term phrase selected as the target term phrase is determined, and the text including the target term phrase and the text of the same type are used as the training input text 16. By doing so, the training input text 16 and the correct answer data 17, that is, the training data 15, are created. In FIG. 21, an example of creating the training input text P−1 and the correct answer data P−1 from the text J−1 and creating the training input text P and the correct answer data P from the text J and the text J+1 among the N texts of the text 1 to text N of the medical document 14 is illustrated.

Embodiment 3_2

Figure 22:
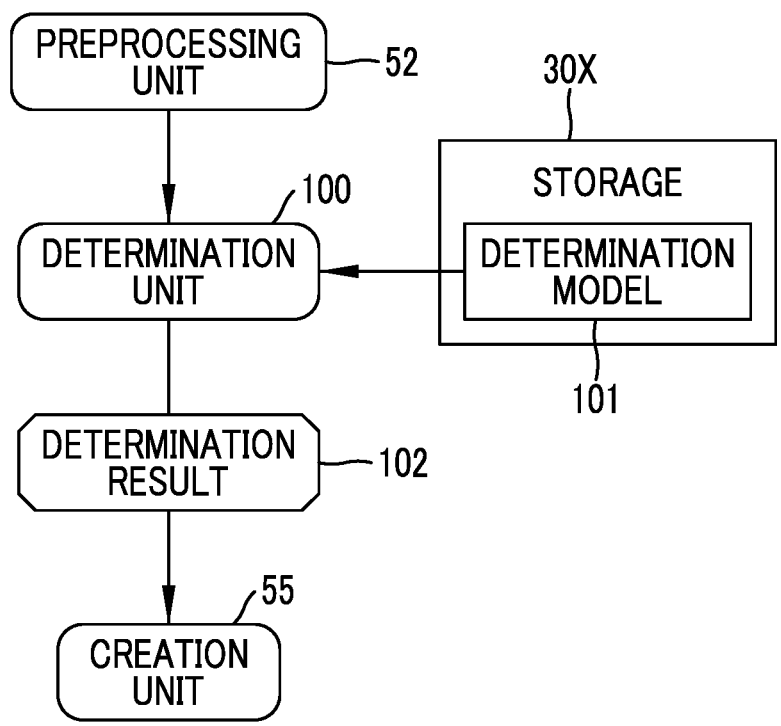
FIG. 22 is a diagram illustrating a processing unit of Embodiment 3_2 including a determination unit that determines which organ a text of a medical document describes.

As illustrated in FIG. 22 as an example, a CPU of a training data creation apparatus of Embodiment 3_2 functions as a determination unit 100 in addition to each of the units 50 to 56 (in FIG. 22, only the preprocessing unit 52 and the creation unit 55 are illustrated) of Embodiment 1. The determination unit 100 determines which organ the text of the medical document 14 describes using a determination model 101 stored in the storage 30X. The determination unit 100 outputs a determination result 102 to the creation unit 55. While illustration is not provided, a determination model 101 is a model created by performing the fine tuning adapted to the determination of the organ on the pretrained natural language processing model on which the pretraining is performed using the training input text 16 created using the typical method of randomly selecting the target term phrase regardless of the degree of association, as in the case of the derivation model 85.

Figure 23:
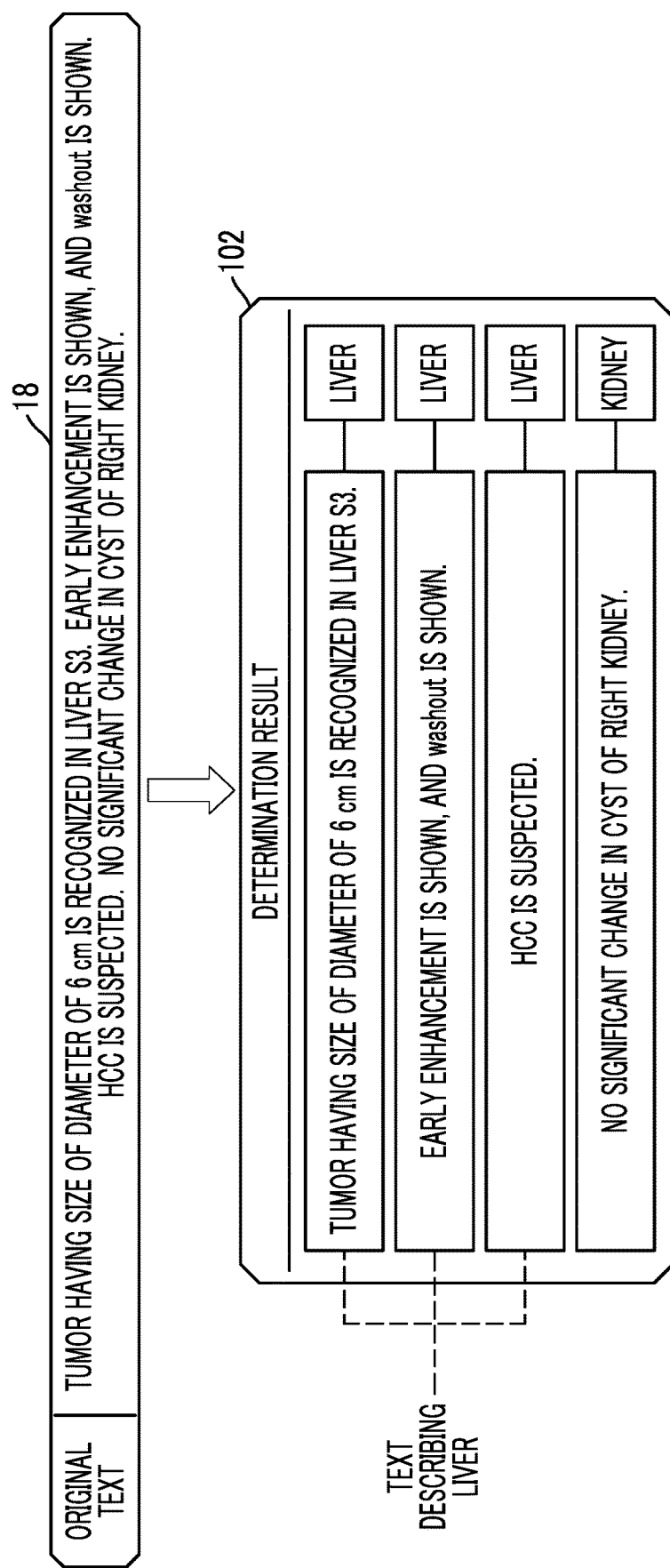
FIG. 23 is a diagram illustrating a determination result.

As illustrated in FIG. 23 as an example, each text of the medical document 14 is labeled with an organ in the determination result 102. In FIG. 23, the original text 18 consisting of four texts "Tumor having a size of a diameter of 6 cm is recognized in a liver S3. Early enhancement is shown, and washout is shown. HCC is suspected. No significant change in a cyst of a right kidney." is illustrated as in the case of Embodiment 3_1. A case where the original text 18 is labeled with the organ is illustrated. That is, "Tumor having a size of a diameter of 6 cm is recognized in a liver S3.", "Early enhancement is shown, and washout is shown.", and "HCC is suspected." are labeled with "liver" as an organ. On the other hand, "No significant change in a cyst of a right kidney." is labeled with "kidney" as an organ. That is, in this case, the determination unit 100 determines that all of three texts "Tumor having a size of a diameter of 6 cm is recognized in a liver S3.", "Early enhancement is shown, and washout is shown.", and "HCC is suspected." are texts describing a liver. The determination model 101 may determine that the organ is not known. In this case, a text for which a determination that the organ is not known is made is not labeled with the organ.

Figure 24:
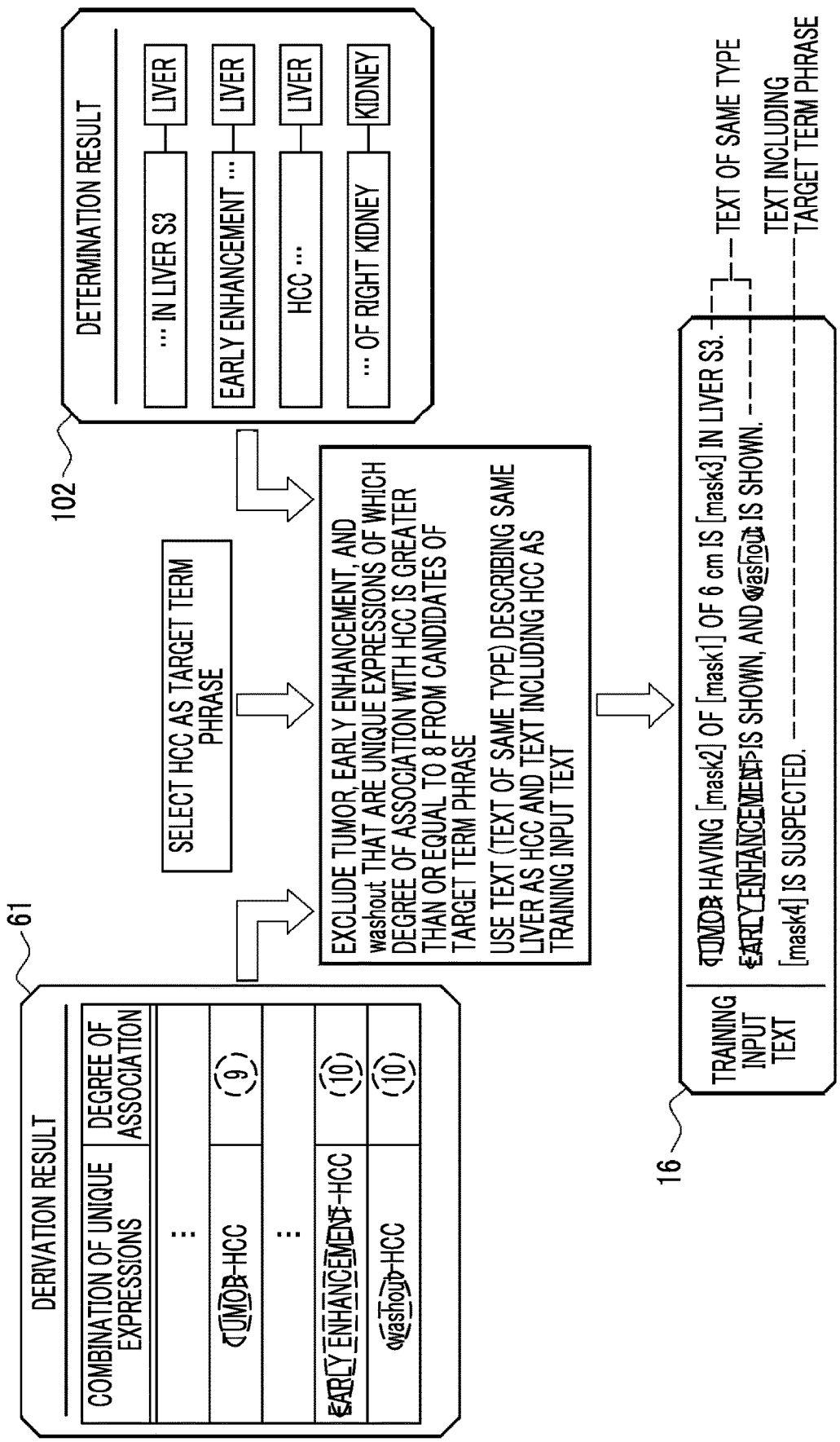
FIG. 24 is a diagram illustrating processing of a creation unit in Embodiment 3_2.

FIG. 24 illustrates a case where "HCC" that is the unique expression is selected as the target term phrase as in the example illustrated in FIG. 11 and the like. In this case, according to the derivation result 61, "tumor", "early enhancement", and "washout" are unique expressions of which the degree of association with "HCC" is greater than or equal to 8. Thus, the creation unit 55 excludes "tumor", "early enhancement", and "washout" from the candidates of the target term phrase. In addition, according to the determination result 102, "Tumor having a size of a diameter of 6 cm is recognized in a liver S3." and "Early enhancement is shown, and washout is shown." are texts describing the same liver as "HCC is suspected." that is a text including "HCC". Thus, the creation unit 55 uses "HCC is suspected.", "Tumor having a size of a diameter of 6 cm is recognized in a liver S3.", and "Early enhancement is shown, and washout is shown." as the training input texts 16 to be collectively input into the natural language processing model 10 at once. Here, "HCC is suspected." is an example of a "text including a term phrase selected as a target term phrase" and a "text including a target term phrase" according to the embodiment of the disclosed technology. In addition, "Tumor having a size of a diameter of 6 cm is recognized in a liver S3." and "Early enhancement is shown, and washout is shown." are an example of a "text of the same type" and a "text describing the same organ as an organ related to a term phrase selected as a target term phrase" according to the embodiment of the disclosed technology.

Figure 25:
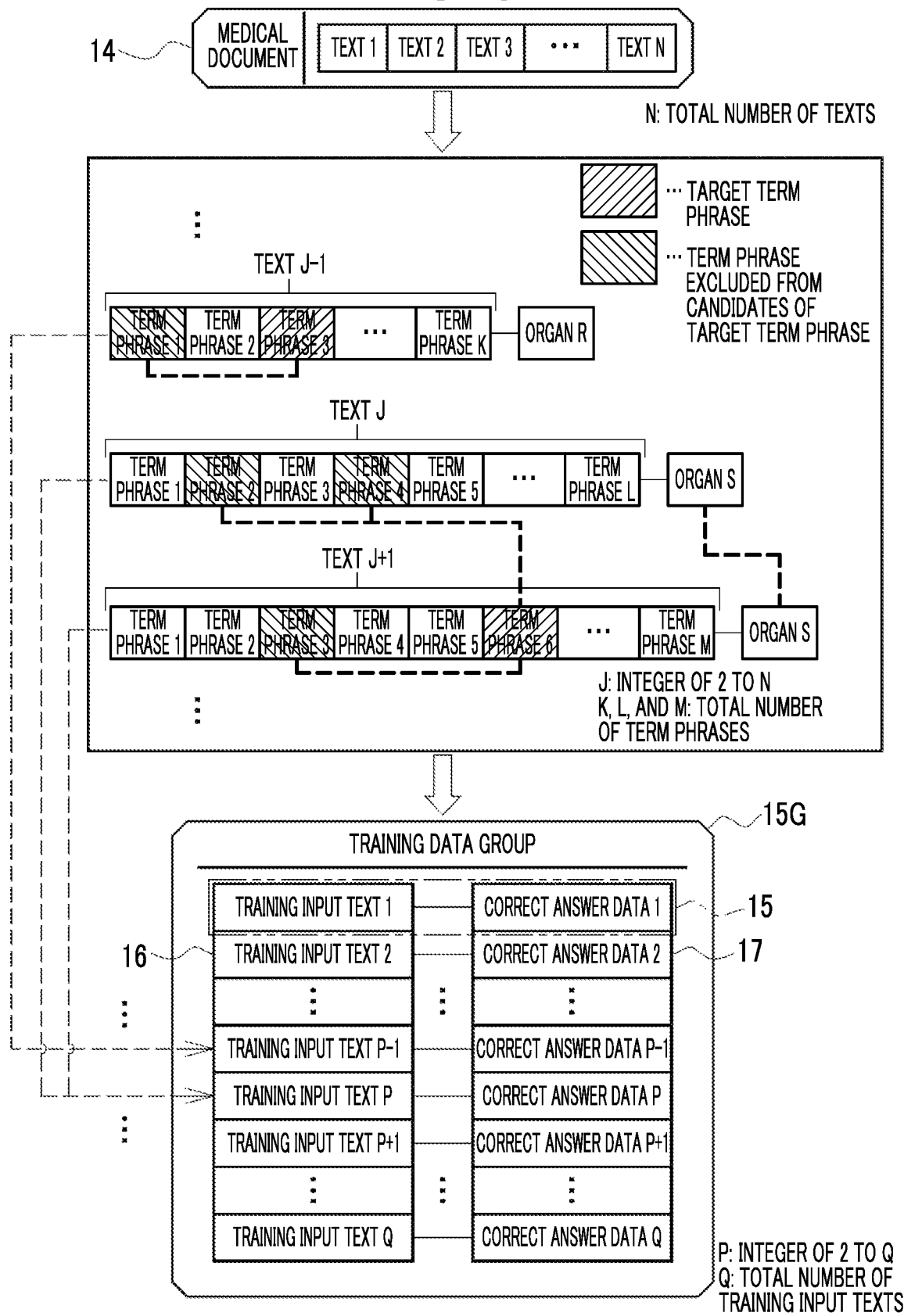
FIG. 25 is a diagram of overall processing of a training data creation apparatus in Embodiment 3_2.

FIG. 25 is a diagram of overall processing of the training data creation apparatus in Embodiment 3_2. In the training data creation apparatus of Embodiment 3_2, first, the unique expressions of each text of the medical document 14 are extracted in the extraction unit 53 as in Embodiment 1. The degree of association among the unique expressions is derived in the derivation unit 54. Furthermore, in the training data creation apparatus of Embodiment 3_2, which organ the text of the medical document 14 describes is determined in the determination unit 100. Last, the target term phrase is selected in the creation unit 55 based on the degree of association. Specifically, at least one unique expression of which the degree of association with the term phrase selected as the target term phrase is greater than or equal to 8 is excluded from the candidates of the target term phrase. In addition, the text including the target term phrase and the text of the same type are used as the training input text 16 in the creation unit 55. By doing so, the training input text 16 and the correct answer data 17, that is, the training data 15, are created. In FIG. 25, an example of creating the training input text P−1 and the correct answer data P−1 from the text J−1 for which a determination is made that the organ is R, and creating the training input text P and the correct answer data P from the text J and the text J+1 for which a determination that the organ is S is made among the N texts of the text 1 to text N of the medical document 14 is illustrated.

In Embodiment 3, the CPU of the training data creation apparatus determines the text of the same type as the text including the term phrase selected as the target term phrase. The text including the target term phrase and the text of the same type are used as the training input text 16. Accordingly, for example, a concern that the training input text 16 including only one text "HCC is suspected." and having "HCC" masked is created and it is difficult to predict the masked term phrase can be reduced. Consequently, it is possible to further contribute to the effective training of the natural language processing model 10.

The CPU of the training data creation apparatus of Embodiment 3_1 determines that a text including the unique expression of which the degree of association with the term phrase selected as the target term phrase satisfies the condition set in advance is the text of the same type. Thus, the unique expression necessary for predicting the term phrase selected as the target term phrase can be left in the training input text 16. Accordingly, a concern that it is difficult to predict the masked term phrase can be reduced. Consequently, it is possible to further contribute to the effective training of the natural language processing model 10.

The document is the medical document 14, and the determination unit 100 determines that a text describing the same organ as the organ related to the term phrase selected as the target term phrase is the text of the same type. Thus, a text highly associated with the text including the target term phrase can be used as the training input texts 16 to be collectively input into the natural language processing model 10 at once. The text of the same type may also be a text describing the same disease name as the disease name related to the term phrase selected as the target term phrase.

Embodiment 4

Figure 26:
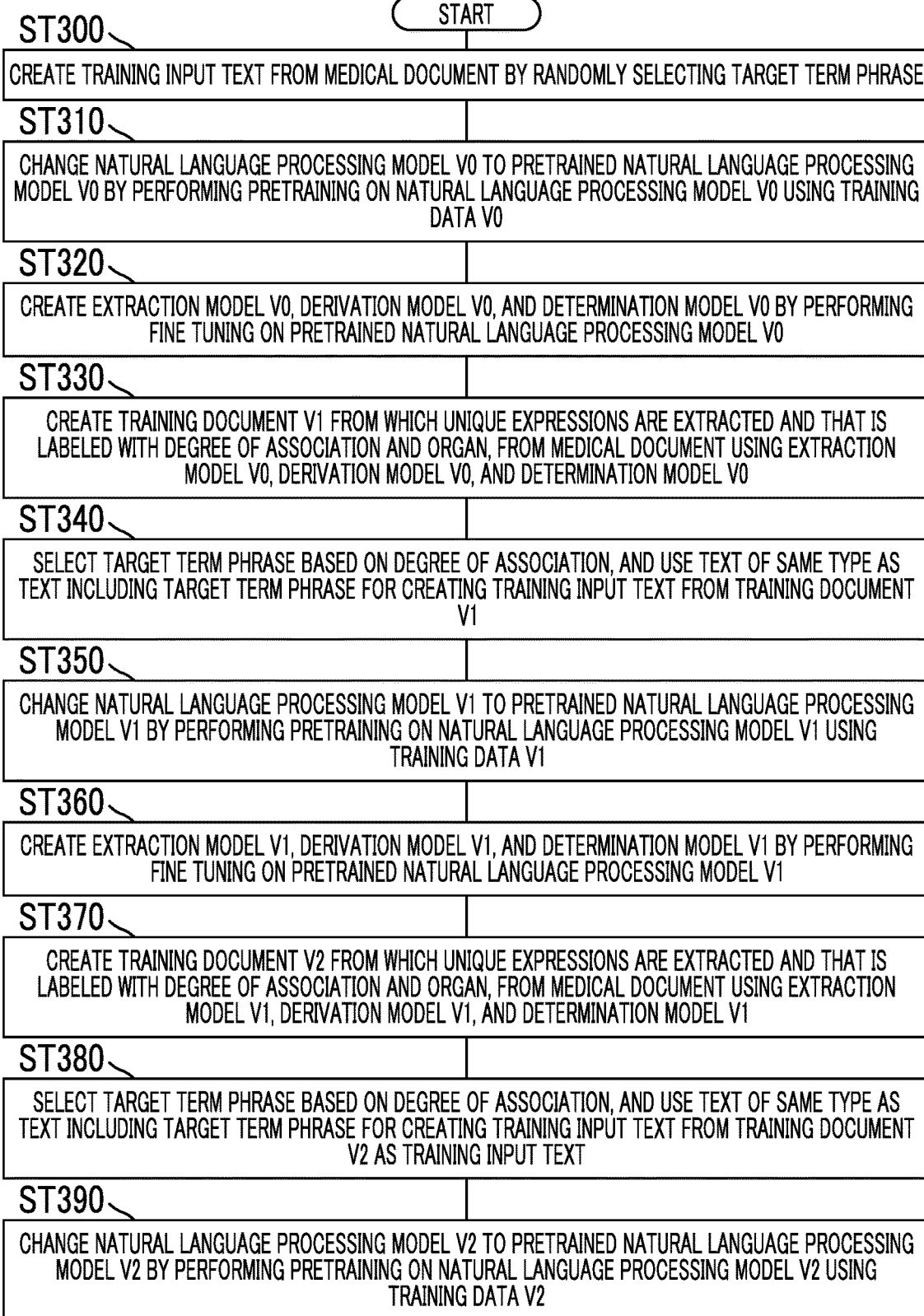
FIG. 26 is a flowchart illustrating a processing procedure of Embodiment 4.
Figure 27:
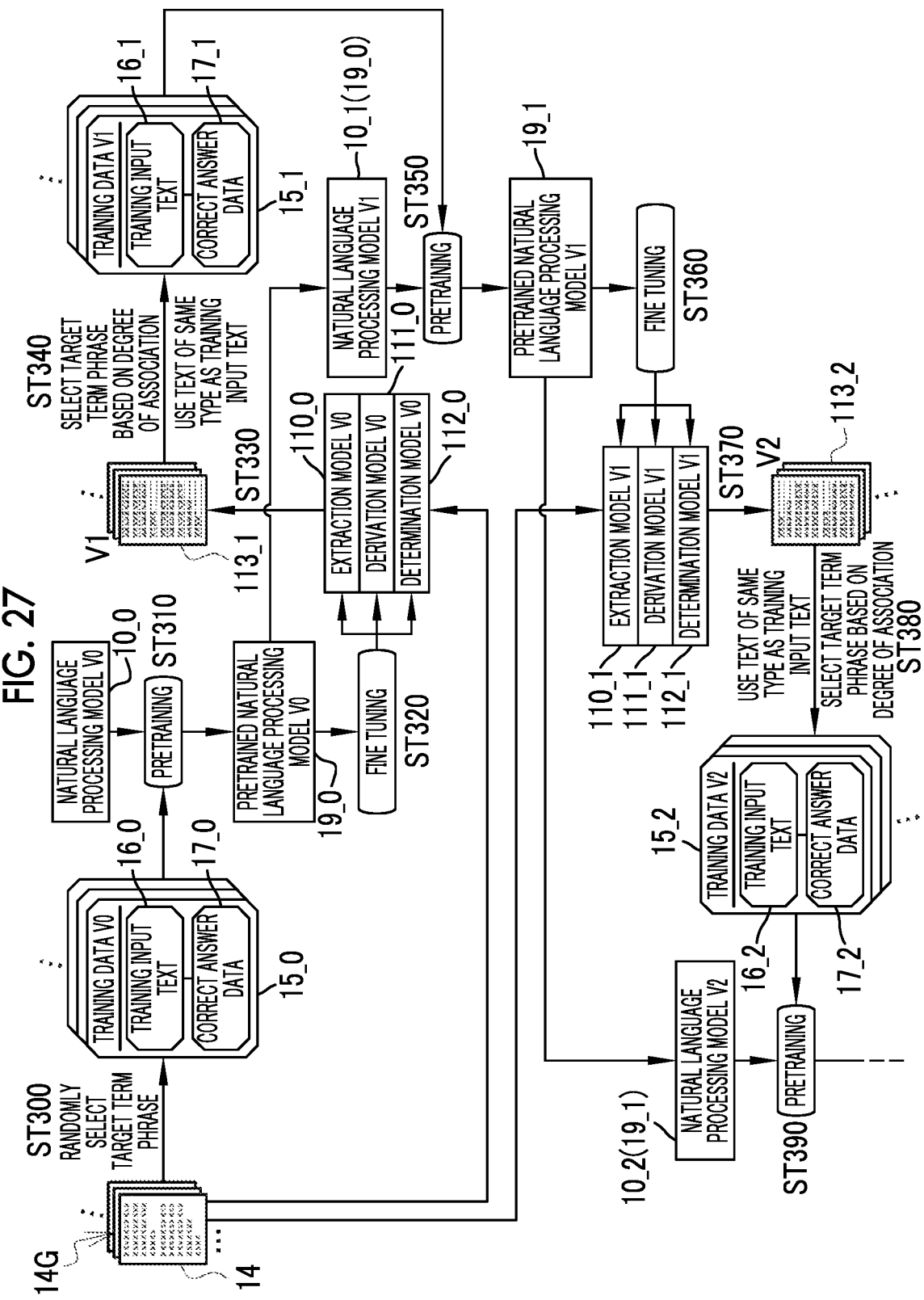
FIG. 27 is a diagram illustrating the processing procedure of Embodiment 4.

In Embodiment 4 illustrated in FIG. 26 and FIG. 27 as an example, a cycle of the following series of processing is repeated.

In Embodiment 4, first, first processing of creating an extraction model 110 for extracting the unique expressions, a derivation model 111 for deriving the degree of association among the unique expressions, and a determination model 112 for determining which organ the text of the medical document 14 describes from the natural language processing model 10 is performed. Next, second processing of creating a training document 113 from which the unique expressions are extracted and that is labeled with the degree of association and the organ, using the extraction model 110, the derivation model 111, and the determination model 112 is performed. Third processing of creating the training input text 16 from the training document 113 created in the second processing using the method according to the embodiment of the disclosed technology is performed. Furthermore, fourth processing of changing the natural language processing model 10 to the pretrained natural language processing model 19 (updating the natural language processing model 10) by performing the pretraining on the natural language processing model 10 using the training input text 16 created in the third processing is performed. In Embodiment 4, a cycle of the first processing to the fourth processing is repeated.

Specifically, as illustrated in FIG. 26 and FIG. 27, first, in an initial cycle, a training input text 16_0 and correct answer data 17_0 are created from the medical document 14 using the typical method of randomly selecting the target term phrase in the CPU of the training data creation apparatus (step ST300). Training data 15_0 that is a set of the training input text 16_0 and the correct answer data 17_0 will be referred to as training data V0.

In the CPU of the training apparatus, a natural language processing model 10_0 (referred to as a natural language processing model V0) is changed to a pretrained natural language processing model 19_0 (referred to as a pretrained natural language processing model V0) by performing the pretraining on the natural language processing model V0 using the training data V0 (step ST310). An extraction model 110_0 (referred to as an extraction model V0), a derivation model 111_0 (referred to as a derivation model V0), and a determination model 112_0 (referred to as a determination model V0) are created by performing the fine tuning on the pretrained natural language processing model V0 (step ST320). Accordingly, the first processing of the initial cycle is completed.

In the CPU of the training data creation apparatus, a training document 113_1 (referred to as a training document V1) from which the unique expressions are extracted and that is labeled with the degree of association and the organ is created from the medical document 14 using the extraction model V0, the derivation model V0, and the determination model V0 (step ST330). Accordingly, the second processing of the initial cycle is completed.

Next, as illustrated in Embodiment 1, the target term phrase is selected based on the degree of association. In addition, as illustrated in Embodiment 3, the text including the target term phrase and the text of the same type are used as a training input text 16_1, and the training input text 16_1 and correct answer data 17_1 are created from the training document V1 (step ST340). Accordingly, the third processing of the initial cycle is completed. Training data 15_1 that is a set of the training input text 16_1 and the correct answer data 17_1 will be referred to as training data V1.

In the CPU of the training apparatus, a natural language processing model 10_1 (referred to as a natural language processing model V1) is changed to a pretrained natural language processing model 19_1 (referred to as a pretrained natural language processing model V1) by performing the pretraining on the natural language processing model V1 using the training data V1 (step ST350). The natural language processing model V1 is the pretrained natural language processing model V0. That is, in step ST350, the pretrained natural language processing model V0 is retrained using the training data V2. Accordingly, the fourth processing of the initial cycle is completed.

An extraction model 110_1 (referred to as an extraction model V1), a derivation model 111_1 (referred to as a derivation model V1), and a determination model 112_1 (referred to as a determination model V1) are created by performing the fine tuning on the pretrained natural language processing model V1 (step ST360). Accordingly, the first processing of a second cycle is completed.

In the CPU of the training data creation apparatus, a training document 113_2 (referred to as a training document V2) from which the unique expressions are extracted and that is labeled with the degree of association and the organ is created from the medical document 14 using the extraction model V1, the derivation model V1, and the determination model V1 (step ST370). Accordingly, the second processing of the second cycle is completed.

Next, as illustrated in Embodiment 1, the target term phrase is selected based on the degree of association. In addition, as illustrated in Embodiment 3, the text including the target term phrase and the text of the same type are used as a training input text 16_2, and the training input text 16_2 and correct answer data 17_2 are created from the training document V2 (step ST380). Accordingly, the third processing of the second cycle is completed. Training data 15_2 that is a set of the training input text 16_2 and the correct answer data 17_2 will be referred to as training data V2.

In the CPU of the training apparatus, a natural language processing model 10_2 (referred to as a natural language processing model V2) is changed to a pretrained natural language processing model 19_2 (referred to as a pretrained natural language processing model V2; not illustrated in FIG. 27) by performing the pretraining on the natural language processing model V2 using the training data V2 (step ST390). The natural language processing model V2 is the pretrained natural language processing model V1. That is, in step ST390, the pretrained natural language processing model V1 is retrained using the training data V2. Accordingly, the fourth processing of the second cycle is completed.

In Embodiment 4, the CPU of the training data creation apparatus and the CPU of the training apparatus create the extraction model 110, the derivation model 111, and the determination model 112 from the natural language processing model 10. Next, the training document 113 from which the unique expressions are extracted and that is labeled with the degree of association and the organ is created using the extraction model 110, the derivation model 111, and the determination model 112, and the training input text 16 is created from the training document 113. Last, the natural language processing model 10 is updated by training the natural language processing model 10 using the created training input text 16. A cycle of this series of processing is repeated.

Thus, performance of the extraction model 110, the derivation model 111, and the determination model 112 is gradually increased through the cycles. Accordingly, extraction accuracy of the unique expressions of the training document 113 and accuracy of labeling with the degree of association and the organ are also gradually increased. Accordingly, the training input text 16 created from the training document 113 also gradually becomes a training input text corresponding to the pretraining. Consequently, performance of the pretrained natural language processing model 19 can be gradually increased.

In the initial cycle, the CPU of the training apparatus creates the extraction model 110_0 and the like from the pretrained natural language processing model 19_0 created by training using the training input text 16 in which the target term phrase is randomly selected regardless of the degree of association. Thus, for example, the training document 113 from which the unique expressions are extracted does not need to be initially manually created, and the effort can be significantly reduced.

The CPU of the training apparatus further creates the derivation model 111 for deriving the degree of association from the pretrained natural language processing model 19. The CPU of the training data creation apparatus creates the training document 113 labeled with the degree of association using the derivation model 111. Thus, an effort of manual labeling with the degree of association can be reduced. In addition, the degree-of-association information 42 illustrated in Embodiment 1 does not need to be used.

The document is the medical document 14, and the CPU of the training apparatus further creates the determination model 112 for determining which organ the text describes from the pretrained natural language processing model 19. The CPU of the training data creation apparatus creates the training document 113 labeled with the organ using the determination model 112. Thus, an effort of manual labeling with the organ can be reduced. The extraction model 110 may be the only model created from the natural language processing model 10 in the first processing.

In each of the embodiments, while the training data creation apparatus creates the training input text 16, and the training apparatus trains the natural language processing model 10, the disclosed technology is not limited thereto. One computer may create the training input text 16 and train the natural language processing model 10.

The degree of association is not limited to the numerical value of 1 to 10 or 0 to 1. The degree of association may be a label such as high, medium, or low. In addition, while the medical document 14 is illustrated as the document, the disclosed technology is not limited thereto. The document may be a novel, a news article, patent literature, or the like. Furthermore, the document may be a document of a narrower field such as a paper related to new coronavirus infection. In addition, while the unique expression is illustrated as the specific term phrase, the disclosed technology is not limited thereto. The specific term phrase may be a term phrase set as a keyword by the operator.

In each of the embodiments, for example, the following various processors can be used as a hardware structure of a processing unit executing various processing of the acquisition units 50 and 75, the RW controllers 51 and 76, the extraction unit 53, the derivation units 54 and 86, the creation unit 55, the distribution controller 56, the pretraining unit 77, the fine tuning unit 78, and the determination unit 100. The various processors include, in addition to the CPUs 32X and 32Y that are general-purpose processors functioning as various processing units by executing software (operation programs 40 and 70) as described above, a programmable logic device (PLD) such as a field programmable gate array (FPGA) that is a processor having a circuit configuration changeable after manufacturing, a dedicated electric circuit such as an application specific integrated circuit (ASIC) that is a processor having a circuit configuration dedicatedly designed to execute specific processing, and the like.

One processing unit may be composed of one of the various processors or may be composed of a combination of two or more processors of the same type or different types (for example, a combination of a plurality of FPGAs and/or a combination of a CPU and an FPGA). In addition, a plurality of processing units may be composed of one processor.

A first example of the plurality of processing units composed of one processor is, as represented by a computer such as a client and a server, a form in which one processor is composed of a combination of one or more CPUs and software, and the processor functions as the plurality of processing units. A second example is, as represented by a system on chip (SoC) or the like, a form of using a processor that implements functions of the entire system including the plurality of processing units in one integrated circuit (IC) chip. Accordingly, various processing units are configured using one or more of the various processors as a hardware structure.

Furthermore, more specifically, an electric circuit (circuitry) in which circuit elements such as semiconductor elements are combined can be used as the hardware structure of the various processors.

Various embodiments and/or various modification examples described above can be appropriately combined in the disclosed technology. In addition, the disclosed technology is not limited to the embodiments and may employ various configurations without departing from the gist thereof. Furthermore, the disclosed technology also applies to, in addition to the program, a storage medium that stores the program in a non-transitory manner.

Above described contents and illustrated contents are detailed descriptions for parts according to the embodiment of the disclosed technology and are merely an example of the disclosed technology. For example, description related to the above configurations, functions, actions, and effects is description related to an example of configurations, functions, actions, and effects of the parts according to the embodiment of the disclosed technology. Thus, apparently, unnecessary parts may be removed, new elements may be added, or parts may be replaced in the above described contents and the illustrated contents without departing from the gist of the disclosed technology. In addition, particularly, description related to common technical knowledge or the like that does not need to be described in terms of embodying the disclosed technology is omitted in the above described contents and the illustrated contents in order to avoid complication and facilitate understanding of the parts according to the embodiment of the disclosed technology.

In the present specification, "A and/or B" has the same meaning as "at least one of A or B". This means that "A and/or B" may be only A, only B, or a combination of A and B. In addition, in the present specification, the same approach as "A and/or B" is applied to a case where three or more matters are represented by connecting the matters with "and/or".

All documents, patent applications, and technical standards disclosed in the present specification are incorporated in the present specification by reference to the same extent as in a case where each of the documents, patent applications, technical standards are specifically and individually indicated to be incorporated by reference.

What is claimed is:

1. An information processing apparatus that creates a training input text which is used for training a natural language processing model and in which a part of term phrases is masked, from a document, the information processing apparatus comprising:
   a processor,
   wherein the processor is configured to train the natural language processing model which is able to predict a part of term phrases which has been masked by:
      extracting a plurality of specific term phrases from the document;
      deriving a degree of association indicating a degree of association among the plurality of specific term phrases;
      selecting a target term phrase that is a term phrase as a target to be masked based on the degree of association;
      determining a text of a same type as a text including the term phrase selected as the target term phrase; and
      using the text including the target term phrase and the text of the same type as the training input text.

2. The information processing apparatus according to claim 1,
   wherein the processor is configured to:
      exclude the specific term phrase of which the degree of association with the term phrase selected as the target term phrase satisfies a condition set in advance, from candidates of the target term phrase.

3. The information processing apparatus according to claim 1,
   wherein the processor is configured to:
      determine that a text including the specific term phrase of which the degree of association with the term phrase selected as the target term phrase satisfies a condition set in advance is the text of the same type.

4. The information processing apparatus according to claim 1,
   wherein the document is a medical document, and
   the processor is configured to:
      determine that a text describing the same organ as an organ related to the term phrase selected as the target term phrase is the text of the same type.

5. The information processing apparatus according to claim 1,
   wherein the processor is configured to:
      derive the degree of association using degree-of-association information in which the degree of association corresponding to a combination of types of the specific term phrases is set in advance.

6. The information processing apparatus according to claim 5,
   wherein the document is a medical document, and
   the types include at least one of an anatomical site, a quantity, a lesion name, a property of a lesion, or a disease name.

7. The information processing apparatus according to claim 1,
   wherein the processor is configured to:
      derive the degree of association using a trained derivation model.

8. The information processing apparatus according to claim 7,
   wherein the derivation model is created based on a trained natural language processing model.

9. The information processing apparatus according to claim 1,
   wherein the processor is configured to:
      train the natural language processing model using the training input text.

10. The information processing apparatus according to claim 9,
    wherein the processor is configured to:
       repeat a cycle of a series of processing including
          creating an extraction model for extracting at least the specific term phrases from the natural language processing model,
          creating a training document from which the specific term phrases are extracted using the extraction model,
          creating the training input text from the training document, and
          updating the natural language processing model by training the natural language processing model using the created training input text.

11. The information processing apparatus according to claim 10,
    wherein the processor is configured to:
       in an initial cycle, create the extraction model from a natural language processing model created by training using a training input text in which the target term phrase is randomly selected regardless of the degree of association.

12. The information processing apparatus according to claim 10,
wherein the processor is configured to:
further create a derivation model for deriving the degree of association from the natural language processing model; and
create the training document labeled with the degree of association using the derivation model.

13. The information processing apparatus according to claim 10,
wherein the document is a medical document, and
the processor is configured to:
further create a determination model for determining which organ a text describes from the natural language processing model; and
create the training document labeled with the organ using the determination model.

14. An operation method of an information processing apparatus that creates a training input text which is used for training a natural language processing model and in which a part of term phrases is masked, from a document, the operation method comprising:
extracting a plurality of specific term phrases from the document;
deriving a degree of association indicating a degree of association among the plurality of specific term phrases;
selecting a target term phrase that is a term phrase as a target to be masked based on the degree of association;
determining a text of a same type as a text including the term phrase selected as the target term phrase; and
using the text including the target term phrase and the text of the same type as the training input text.

15. A non-transitory computer-readable storage medium storing an operation program of an information processing apparatus that creates a training input text which is used for training a natural language processing model and in which a part of term phrases is masked, from a document, the operation program causing a computer to execute a process to train the natural language processing model which is able to predict the part of term phrases which is masked, the process comprising:
extracting a plurality of specific term phrases from the document;
deriving a degree of association indicating a degree of association among the plurality of specific term phrases;
selecting a target term phrase that is a term phrase as a target to be masked based on the degree of association;
determining a text of a same type as a text including the term phrase selected as the target term phrase; and
using the text including the target term phrase and the text of the same type as the training input text.

* * * * *